(12) United States Patent
Kim

(10) Patent No.: US 12,014,688 B2
(45) Date of Patent: Jun. 18, 2024

(54) DISPLAY DEVICE HOLDING A SENSING SIGNAL VOLTAGE OF AT LEAST TWO SENSING SIGNALS IN A SAMPLING CAPACITOR DURING A READ PERIOD

(71) Applicant: SAMSUNG DISPLAY CO., LTD., Yongin-si (KR)

(72) Inventor: Chul Kim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 18/109,330

(22) Filed: Feb. 14, 2023

(65) Prior Publication Data
US 2024/0029658 A1 Jan. 25, 2024

(30) Foreign Application Priority Data
Jul. 22, 2022 (KR) .................. 10-2022-0091208

(51) Int. Cl.
*G09G 3/3266* (2016.01)
*G09G 3/20* (2006.01)
*G09G 3/3233* (2016.01)

(52) U.S. Cl.
CPC ......... *G09G 3/3266* (2013.01); *G09G 3/2096* (2013.01); *G09G 3/3233* (2013.01); *G09G 2300/0426* (2013.01); *G09G 2300/0819* (2013.01); *G09G 2300/0842* (2013.01); *G09G 2310/0202* (2013.01); *G09G 2310/0291* (2013.01); *G09G 2310/08* (2013.01); *G09G 2360/14* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 10,398,324 B2 | 9/2019 | Mukkamala et al. | |
| 11,158,258 B2 | 10/2021 | Cha et al. | |
| 11,179,047 B2 | 11/2021 | Mukkamala et al. | |
| 2014/0168148 A1* | 6/2014 | Kang | G06F 3/0446 345/174 |
| 2016/0180138 A1* | 6/2016 | Riedijk | G01R 27/2605 324/686 |
| 2018/0004353 A1* | 1/2018 | Shin | G02F 1/1343 |

(Continued)

FOREIGN PATENT DOCUMENTS

KR 10-2021-0064483 6/2021

*Primary Examiner* — Amr A Awad
*Assistant Examiner* — Donna V Bocar
(74) *Attorney, Agent, or Firm* — F. Chau & Associates, LLC

(57) ABSTRACT

A display device including: a display panel including scan write lines, sensing lines, pixels respectively connected to the scan write lines, and optical sensors respectively connected to the scan write lines and the sensing lines; a scan driver configured to sequentially output scan write signals to the scan write lines in response to a scan control signal; a read-out circuit configured to receive light sensing signals of the optical sensors from the sensing lines in response to a first sampling signal; and a timing controller configured to control the scan driver and the read-out circuit, wherein an interval between pulses of the first sampling signal has a first horizontal period, and an interval between pulses of each of the scan write signals has a second horizontal period.

13 Claims, 21 Drawing Sheets

300: 310, 320, 330
PS: PS1, PS2
LSS: LSS1, LSS2

(56) References Cited

U.S. PATENT DOCUMENTS

| | | | |
|---|---|---|---|
| 2020/0159385 A1* | 5/2020 | Chung | G06F 3/042 |
| 2020/0166658 A1* | 5/2020 | Duan | G01T 1/247 |
| 2021/0036046 A1* | 2/2021 | Kwon | G06V 30/333 |
| 2021/0158751 A1* | 5/2021 | Cha | G06V 40/1318 |
| 2022/0067340 A1* | 3/2022 | Han | H10K 50/865 |
| 2022/0199876 A1* | 6/2022 | Choi | G09G 3/3233 |

* cited by examiner

300: 310, 320, 330
PS: PS1, PS2, PS3, PS4
LSS: LSS1, LSS2, LSS3, LSS4

300: 310, 320, 330

DISPLAY DEVICE HOLDING A SENSING SIGNAL VOLTAGE OF AT LEAST TWO SENSING SIGNALS IN A SAMPLING CAPACITOR DURING A READ PERIOD

CROSS-REFERENCE TO RELATED APPLICATION

This application claims priority under 35 U.S.C. § 119 to Korean Patent Application No. 10-2022-0091208 filed on Jul. 22, 2022 in the Korean Intellectual Property Office, the disclosure of which is incorporated by reference herein in its entirety.

1. Technical Field

The present disclosure relates to a display device.

2. Description of the Related Art

A display device, which is an output device for displaying images, is currently used in various devices. For example, display devices are employed in various electronic devices such as smartphones, digital cameras, laptop computers, tablet personal computers (tablet PCs), navigation devices, and smart televisions. In the case of portable display devices such as smartphones, tablet PCs, and the like, various functions such as image capturing, fingerprint recognition, facial recognition, and the like are provided.

Recently, methods have been developed to more easily obtain biometric information related to health characteristics of a user. For example, attempts have been made to replace a traditional blood pressure measuring device that uses an oscillometric method with a portable blood pressure measuring device.

However, the portable blood pressure measuring device generally requires its own separate light source, sensor, and display, and it must be accompanied by the user's portable smartphone or tablet PC, which can be inconvenient.

SUMMARY

Embodiments of the present disclosure provide a display device capable of detecting light sensing signals at a high speed and at a frequency equal or similar to the driving frequency of an image display panel, and detecting pulse wave signals according to the light sensing signals without an error according to the frequency or the detection speed of the light sensing signals.

According to an embodiment of the disclosure, there is provided a display device including: a display panel including scan write lines, sensing lines, pixels respectively connected to the scan write lines, and optical sensors respectively connected to the scan write lines and the sensing lines; a scan driver configured to sequentially output scan write signals to the scan write lines in response to a scan control signal; a read-out circuit configured to receive light sensing signals of the optical sensors from the sensing lines in response to a first sampling signal; and a timing controller configured to control the scan driver and the read-out circuit, wherein an interval between pulses of the first sampling signal has a first horizontal period, and an interval between pulses of each of the scan write signals has a second horizontal period.

The first horizontal period is longer than the second horizontal period.

Each of the optical sensors includes: a photoelectric conversion element including an anode electrode and a cathode electrode connected to a voltage line; a first sensing transistor including a gate electrode connected to the anode electrode of the photoelectric conversion element; a reset transistor configured to connect a reset voltage line to the anode electrode of the photoelectric conversion element in response to a reset signal; and a second sensing transistor configured to connect the first sensing transistor to a corresponding one of the sensing lines in response to the scan write signal input thereto.

The display device may further include a reset driver configured to output the reset signal for turning on each reset transistor of the optical sensors.

The read-out circuit includes: an amplifier connected to the corresponding one of the sensing lines and comprising an operational amplifier; a sampling unit comprising a first sampling capacitor configured to hold a voltage of one of the light sensing signals in response to the first sampling signal; and an analog-digital (AD) converter configured to convert the held light sensing signal voltage into digital data.

Each of the second sensing transistors is turned on in response to a corresponding one of the scan write signals to output a sensing signal voltage through the sensing line to which it is connected, and each of the sensing signal voltages is held in the first sampling capacitor in response to the first sampling signal.

The first sampling signal has a first period in which the first sampling capacitor is turned on and a second period in which the first sampling capacitor is turned off.

In the first period, the first sampling capacitor accumulates and holds at least two sensing signal voltages among the sensing signal voltages.

The first period is longer than the second horizontal period.

The sampling unit further includes a second sampling capacitor configured to hold a noise voltage in response to a second sampling signal, and the second sampling signal and the first sampling signal are sequentially turned on.

An interval between pulses of each of the second sampling signals is equal to the first horizontal period.

The optical sensors include a first optical sensor and a second optical sensor, and the scan write lines include: a first scan write line configured to provide an $n^{th}$ scan write signal (n being a positive integer) to the pixel connected to the first optical sensor and the first optical sensor; and a second scan write line configured to provide an $(n+1)^{th}$ scan write signal to the pixel connected to the second optical sensor and the second optical sensor, wherein the second horizontal period between the $n^{th}$ scan write signal and the $(n+1)^{th}$ scan write signal is shorter than the first horizontal period of the first sampling signal.

The timing controller outputs a first sampling signal having a turn-on voltage during a first period in a first mode for detecting a fingerprint and having a turn-on voltage during a second period in a second mode for detecting a blood pressure, and the first period is shorter than the second period.

The first period is shorter than the second horizontal period.

The second horizontal period is shorter than the second period.

According to an embodiment of the disclosure, there is provided a display device including: a display panel including a pixel, a first optical sensor, and a second optical sensor; first scan write lines configured to provide a first scan write signal to the pixel and the first optical sensor; second scan write lines configured to provide a second scan write signal to the pixel and the second optical sensor; a scan driver configured to output the first scan write signal to the first scan write lines and the second scan write signal to the second scan write lines; a read-out circuit configured to receive a first light sensing signal from the first optical sensor through a first sensing line in response to a first sampling signal, and receive a second light sensing signal from the second light sensor through a second sensing line; and a timing controller configured to output the first sampling signal to the read-out circuit, wherein the first sampling signal has a first horizontal period, and a pulse width of each of the first scan write signal and the second scan write signal has a second horizontal period.

The first horizontal period is longer than the second horizontal period.

The first sampling signal has a first period having a turn-on voltage and a second period having a turn-off voltage, and the read-out circuit is configured to accumulate and receive the first and second light sensing signals in the first period.

The first period is longer than the second horizontal period.

The read-out circuit includes: an amplifier connected to the first and second sensing lines and comprising an operational amplifier; a sampling unit comprising a first sampling capacitor configured to accumulate and hold voltages of the first and second light sensing signals during the first period of the first sampling signal; and an AD converter configured to convert the held voltages of the first and second light sensing signals into digital data.

According to an embodiment of the disclosure, there is provided a display device including: a display panel including scan write lines, sensing lines, pixels respectively connected to the scan write lines, and optical sensors respectively connected to the scan write lines and the sensing lines; a scan driver configured to sequentially output scan write signals to the scan write lines in response to a scan control signal; a read-out circuit configured to receive light sensing signals of the optical sensors from the sensing lines in response to a first sampling signal; and a timing controller configured to control the scan driver and the read-out circuit, wherein the first sampling signal has a first horizontal period, and each of the scan write signals has a second horizontal period, wherein the first and second horizontal periods overlap each other and the first horizontal period is longer than the second horizontal period.

In accordance with the display device according to one embodiment of the present disclosure, it is possible to prevent detection waveform distortion of the light sensing signals by detecting the light sensing signals at a frequency equal to the driving frequency of the image display panel. Further, it is possible to increase the reliability of a blood pressure detection function by accurately detecting the pulse wave signals according to the light sensing signals without an error according to the detection frequency or the detection speed of the light sensing signals.

BRIEF DESCRIPTION OF THE DRAWINGS

The above and other features of the present disclosure will become more apparent by describing in detail embodiments thereof with reference to the attached drawings, in which.

DETAILED DESCRIPTION OF THE EMBODIMENTS

The present disclosure will now be described more fully hereinafter with reference to the accompanying drawings, in which embodiments thereof are shown. This disclosure may, however, be embodied in different forms and should not be construed as limited to the embodiments set forth herein.

It will be understood that when a layer is referred to as being "on" another layer or substrate, it can be directly on the other layer or substrate, or intervening layers may also be present. The same reference numbers may indicate the same components throughout the specification.

It will be understood that, although the terms "first," "second," etc. may be used herein to describe various elements, these elements should not be limited by these terms. These terms are used to distinguish one element from another element. For instance, a first element discussed below could be termed a second element. Similarly, the second element could also be termed the first element.

Each of the features of the various embodiments of the present disclosure may be combined or combined with each other, in part or in whole, and technically various interlocking and driving are possible. Each embodiment may be implemented independently of each other or may be implemented together in an association.

Figure 1:
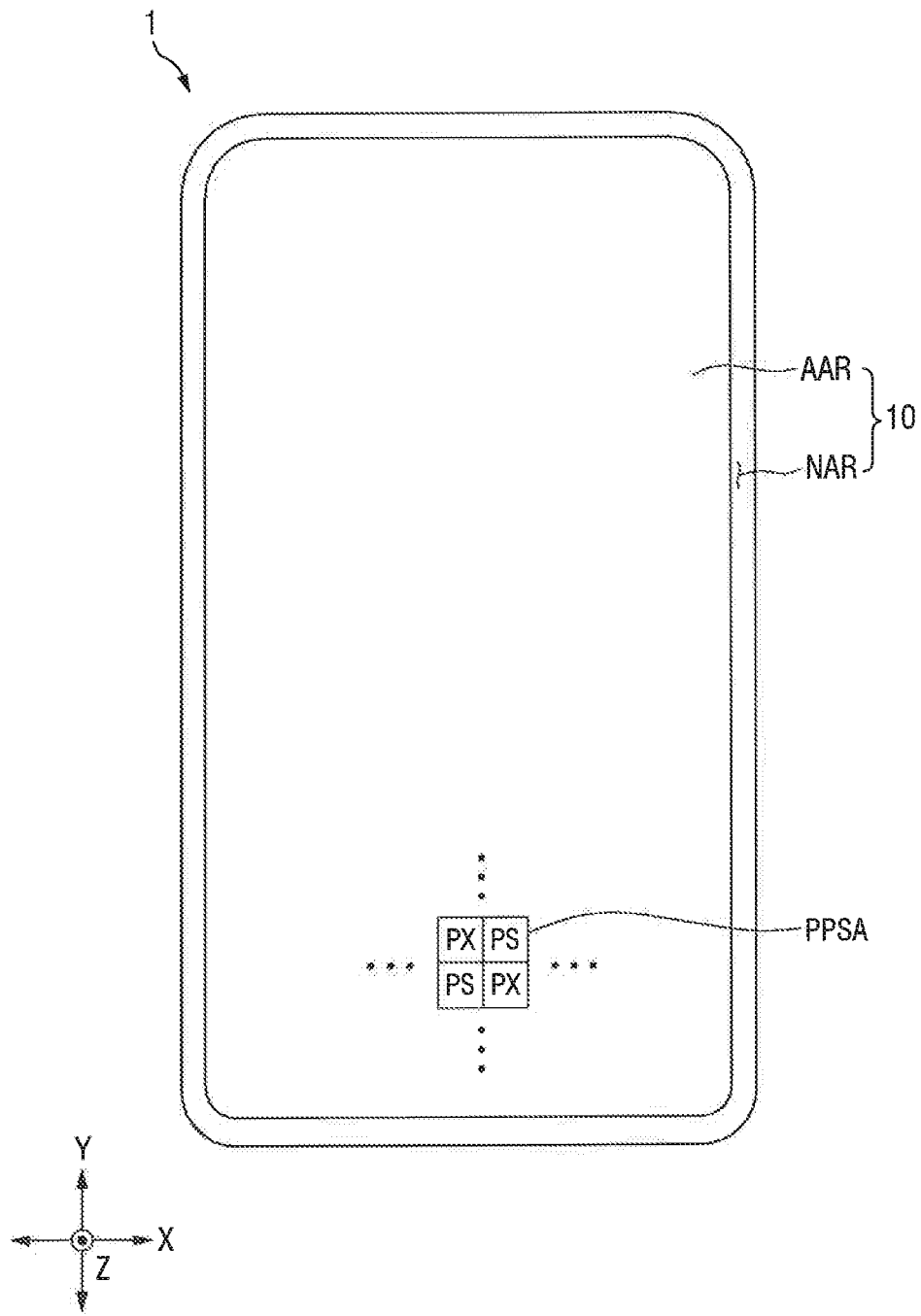
FIG. 1 is a plan view illustrating a display device according to one embodiment of the present disclosure.
Figure 2:
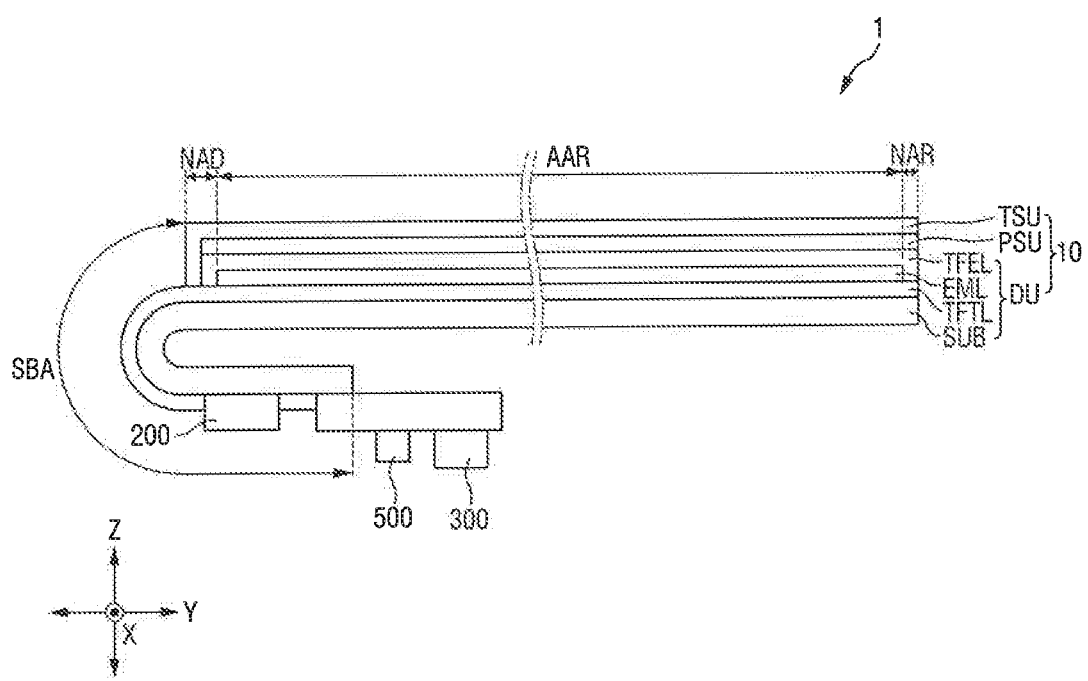
FIG. 2 is a cross-sectional view illustrating a display device according to one embodiment of the present disclosure.

FIG. 1 is a plan view illustrating a display device according to one embodiment of the present disclosure. FIG. 2 is a cross-sectional view illustrating a display device according to one embodiment of the present disclosure.

In FIG. 1, a first direction X, a second direction Y, and a third direction Z are indicated. The first direction X may be a direction parallel to one side of a display device 1 in a plan view and may be, for example, a horizontal direction of the display device 1. A second direction Y may be a direction parallel to another side in contact with the one side of the display device 1 in a plan view and may be, for example, a vertical direction of the display device 1. Hereinafter, for simplicity of description, it is assumed that one side of the first direction X refers to a rightward direction in a plan view, the other side of the first direction X refers to a leftward direction in a plan view, one side of the second direction Y refers an upward direction in a plan view, and the other side of the second direction Y refers to a downward direction in a plan view, respectively. The third direction Z may be a thickness direction of the display device 1. It should be understood, however, that a direction mentioned in the present embodiment is a relative direction and the embodiment is not limited to the direction mentioned.

Referring to FIG. 1, the display device 1 may include various electronic devices that provide a display screen. Examples of the display device 1 may include, but not limited to, a mobile phone, a smart phone, a tablet personal computer (PC), a mobile communication terminal, an electronic notebook, an electronic book, a personal digital assistant (PDA), a portable multimedia player (PMP), a navigation device, an ultra-mobile PC (UMPC), a television, a game console, a wrist watch type electronic device, a head-mounted display, a personal computer monitor, a laptop computer, a car dashboard, a digital camera, a camcorder, an external billboard, an electric billboard, various medical devices, various inspection devices, various home appliances including a display area such as a refrigerator or a washing machine, an Internet-of-Things (IoT) device, and the like. A typical example of the display device 1 to be described later may be a smart phone, a tablet PC, or a laptop computer, but is not limited thereto.

The display device 1 includes a display panel 10 having an active region AAR and a non-active region NAR.

The active region AAR includes a display area on which a screen is displayed. The active region AAR may completely overlap the display area. A plurality of pixels PX for displaying an image may be disposed in the display area. Each pixel PX may include a light emitting element ('EL' in FIG. 6).

The active region AAR further includes a light sensing area PPSA. The light sensing area PPSA is a region that reacts to light, and is configured to sense the amount or wavelength of incident light. The light sensing area PPSA may overlap the display area. Although it is illustrated in FIG. 1 that the light sensing area PPSA is disposed in the lower central area of the active region AAR, the present disclosure is not limited thereto. For example, the light sensing area PPSA may also be provided as an area completely identical to the display area in a plan view. As another example, the light sensing area PPSA may be disposed only in a limited area required for blood pressure measurement. In this case, the light sensing area PPSA may overlap only a part of the display area and not overlap another part of the display area.

A plurality of optical sensors PS that react to light may be disposed in the light sensing area PPSA. Each optical sensor PS may include a photoelectric conversion element 'PD' in FIG. 6 that detects incident light and converts the detected light into an electrical signal.

The non-active region NAR is disposed around the active region AAR. The non-active region NAR may be a bezel area. The non-active region NAR may surround all sides (e.g., four sides in FIG. 1) of the active region AAR, but is not limited thereto.

In the non-active region NAR, signal lines or driving circuits for applying a signal to the active region AAR may be disposed. Further, in the non-active region NAR, driving circuits or signal lines for applying a signal to the light sensing area PPSA and light sensing lines for transmitting an electrical signal from the light sensing area PPSA may be disposed. The non-active region NAR may not include the display area. Furthermore, the non-active region NAR may not include the light sensing area PPSA. In other embodiments, the non-active region NAR may include a part of the light sensing area PPSA. The non-active region NAR may be completely the same as a non-display area where a screen image is not displayed.

Referring further to FIG. 2, the display device 1 includes a display panel 10, a display driving circuit 200, a touch sensing unit TSU, a pressure sensing unit PSU, a read-out circuit 300, and a touch driver 500.

A sub-region SBA may protrude from one side of the non-active region NAR in the second direction Y. The length of the sub-region SBA in the second direction Y may be less than the length of the non-active region NAR in the second direction Y. The length of the sub-region SBA in the first direction X may be substantially equal to or less than the length of the non-active region NAR in the first direction X.

The display driving circuit 200 may be arranged in the sub-region SBA. The display driving circuit 200 may be attached to driving pads using a conductive adhesive member such as an anisotropic conductive film. The sub-region SBA may be bent, and in this case, the sub-region SBA may be disposed under the active region AAR. The sub-region SBA may overlap the active region AAR in the third direction Z.

The pressure sensing unit PSU for sensing a pressure applied by a body part such as a finger or the like may be disposed on the front surface of the display panel 10. The pressure sensing unit PSU, which is formed of a transparent sheet in which a plurality of transparent electrodes are arranged in vertical and horizontal directions, may be disposed on the front surface of the non-active region NAR.

The touch sensing unit TSU for sensing a body part such as a finger or the like may be disposed on the front surface of the pressure sensing unit PSU as well as the active region AAR. The touch sensing unit TSU may include a plurality of touch electrodes to sense a user's touch in a capacitance manner.

The touch sensing unit TSU includes a plurality of touch electrodes arranged to intersect each other in the first direction X and the second direction Y. For example, the plurality of touch electrodes include a plurality of driving electrodes spaced apart from each other side by side in the first direction X, and a plurality of sensing electrodes spaced apart from each other side by side in the second direction Y while intersecting the plurality of driving electrodes with an organic material layer or an inorganic material layer interposed therebetween. The plurality of driving electrodes and the plurality of sensing electrodes may extend to a wiring area (or an image non-display area in which a wire is formed) between display pixels and optical sensors without overlapping the pixels PX and the optical sensors PS arranged in the active region AAR. The plurality of driving electrodes and the plurality of sensing electrodes form a mutual capacitance, and transmit touch sensing signals that vary according to a user's touch to the touch driver 500.

The touch driver 500 may supply touch driving signals to the plurality of driving electrodes, and may receive the touch sensing signals from the plurality of sensing electrodes. The touch driver 500 may detect a change in the mutual capacitance between the plurality of driving electrodes and the plurality of sensing electrodes according to a change in the magnitude of the touch sensing signal. Further, touch data according to the change in the mutual capacitance, coordinate data of a position where a touch is sensed, and the like may be supplied to the display driving circuit 200.

The pressure sensing unit PSU includes a plurality of pressure sensing electrodes intersecting each other in the first direction X and the second direction Y. For example, the plurality of pressure sensing electrodes include a plurality of lower electrodes spaced apart from each other side by side in the first direction X, and a plurality of upper electrodes spaced apart from each other side by side in the second direction Y while intersecting the plurality of lower electrodes with a transparent inorganic (or organic) material layer interposed therebetween. The plurality of lower electrodes and the plurality of upper electrodes may extend to the wiring area (or the image non-display area in which a line is formed) between the display pixels and the optical sensors without overlapping the display pixels and the optical sensors arranged in the active region AAR. The plurality of lower electrodes and the plurality of upper electrodes form a self-capacitance with a transparent inorganic (or organic) material layer interposed therebetween, and transmit pressure sensing signals that vary according to a user's touch pressure to the touch driver 500.

The touch driver 500 may receive the pressure sensing signals from the plurality of lower electrodes or the plurality of upper electrodes, and may sense a change in the self-capacitance using the pressure sensing signals. Accordingly, the touch driver 500 may supply pressure data according to the amount of change in the self-capacitance and sensing coordinate data of a position where a touch is sensed to the display driving circuit 200.

A circuit board may be attached to one end of the sub-region SBA. Thus, the circuit board may be electrically connected to the display panel 10 and the display driving circuit 200. The display panel 10 and the display driving circuit 200 may receive digital video data, timing signals, and driving voltages through the circuit board. The circuit board may be a flexible printed circuit board, a printed circuit board, or a flexible film such as a chip on film.

The display driving circuit 200 may generate electrical control signals and digital data for driving the display panel 10. Each of the display driving circuit 200, the read-out circuit 300, and the touch driver 500 may be formed as an integrated circuit (IC). Each of the display driving circuit 200, the read-out circuit 300, and the touch driver 500 may be attached onto the display panel 10 or the circuit board by a chip on glass (COG) method, a chip on plastic (COP) method, or an ultrasonic bonding method, but the present disclosure is not limited thereto. For example, the display driving circuit 200, the read-out circuit 300, and the touch driver 500 may be attached onto the circuit board by a chip on film (COF) method.

FIG. 2 further show that the display panel 10 includes a display module DU having a substrate SUB, a thin film transistor layer TFTL, a light emitting element layer EML, and an encapsulation layer TFEL.

Figure 3:
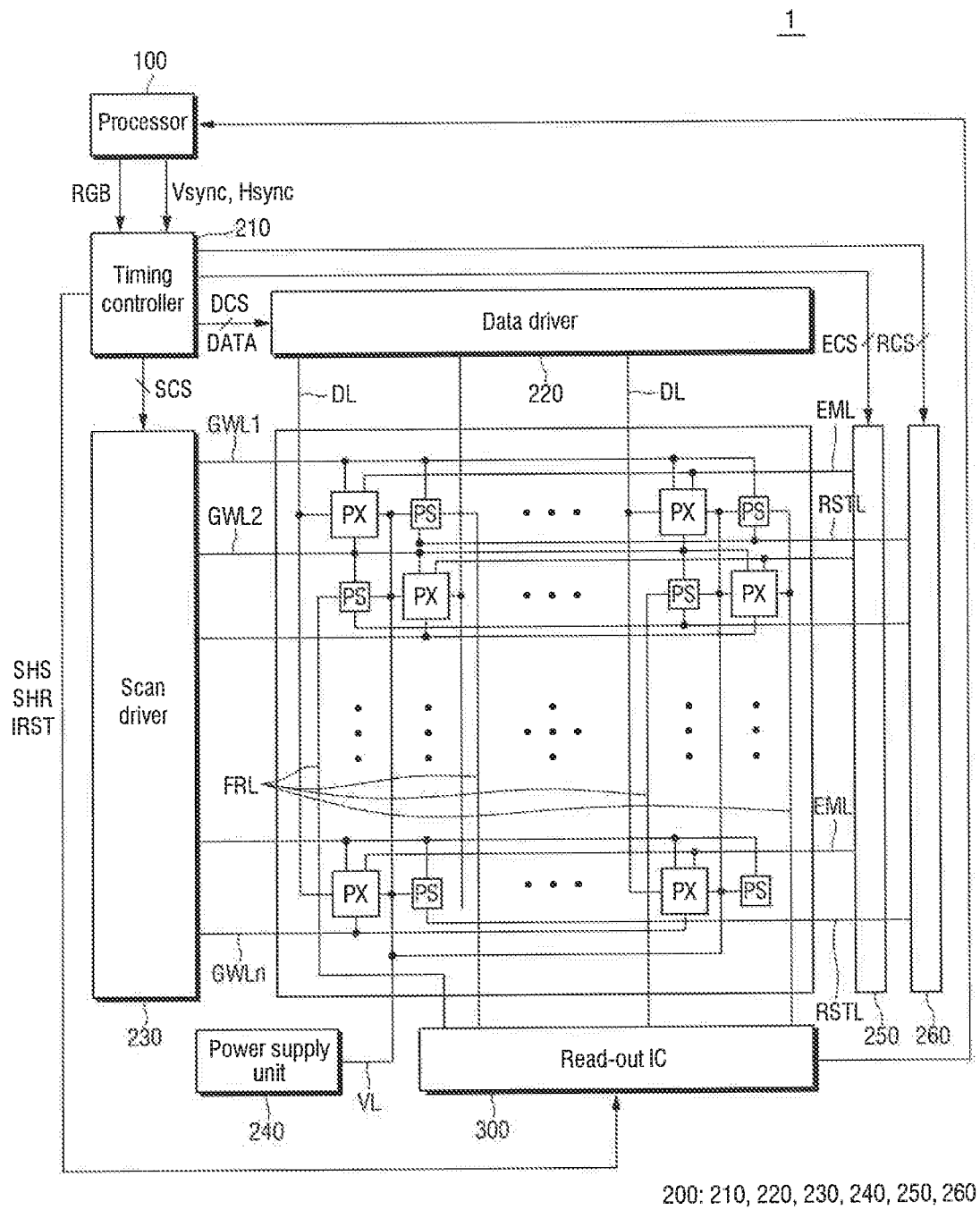
FIG. 3 is a block diagram illustrating a display device according to one embodiment of the present disclosure.
Figure 4:
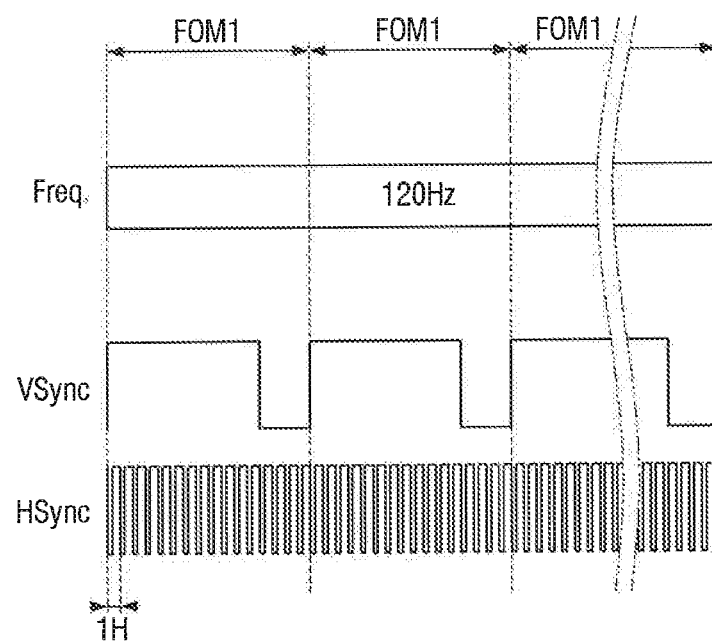
FIG. 4 is a timing diagram illustrating a driving period of a display device according to one embodiment of the present disclosure.

FIG. 3 is a block diagram illustrating a display device according to one embodiment of the present disclosure. FIG. 4 is a timing diagram illustrating a driving period of a display device according to one embodiment of the present disclosure.

The display device 1 according to the present embodiment includes a processor 100, the display driving circuit 200, and the read-out circuit 300.

Referring to FIG. 3, the processor 100 supplies a plurality of control signals and an image signal RGB supplied from the outside to a timing controller 210. The processor 100 may further include a graphic processing unit (hereinafter, referred to as GPU) that provides graphics for the image signal RGB provided from the outside. The image signal RGB, which is an image source that has been subjected to graphic processing in the GPU, may be provided to the timing controller 210. The image signal RGB may have a frequency of 120 Hz, for example.

In the display device 1 according to the present embodiment, the plurality of control signals may include a vertical synchronization signal Vsync, a horizontal synchronization signal Hsync, a clock signal, an enable signal, and the like.

Referring further to FIG. 4, the vertical synchronization signal Vsync defines frame periods. The vertical synchronization signal Vsync includes a high period and a low period for each period, and the period of the vertical synchronization signal Vsync corresponds to a frame frequency of each period. For example, the vertical synchronization signal Vsync may define a plurality of frame periods FMO1 having a first frame frequency. For example, the first frame frequency may be 120 Hz. Accordingly, the period of the vertical synchronization signal Vsync may be 33.2 ms.

The horizontal synchronization signal Hsync defines horizontal periods in one frame period. The horizontal synchronization signal Hsync includes a high period and a low period for each period, and the period of the horizontal synchronization signal Hsync corresponds to each of the horizontal periods. For example, the first horizontal synchronization signal Hsync1 may define first horizontal periods 1H. For example, the period of the first horizontal synchronization signal Hsync1 may be 3.2 µs.

Referring back to FIG. 3, the display driving circuit 200 may generate voltages and signals for driving the optical sensors PS and the pixels PX of the display panel 10. The display driving circuit 200 may be an integrated circuit (IC) and attached on the circuit board by a chip on film (COF) method, but is not limited thereto, and may be attached on the non-active region NAR of the display panel 10 in a chip on glass (COG) method, a chip on plastic (COP) method or an ultrasonic bonding method.

The display driving circuit 200 includes a data driver 220 for driving the pixels PX of the display panel 10, a scan driver 230 for driving the pixels PX and the optical sensors PS, and the timing controller 210 for controlling the driving timings of the data driver 220 and the scan driver 230. In addition, the display driving circuit 200 may further include a power supply unit 240, an emission driver 250, and a reset driver 260.

The timing controller 210 receives the image signal RGB, the vertical synchronization signal Vsync, and the horizontal synchronization signal Hsync supplied from the outside of the display device 1. The timing controller 210 may output image data DATA and a data control signal DCS to the data driver 220. Further, the timing controller 210 may generate a scan control signal SCS for controlling the operation timing of the scan driver 230, an emission control signal ECS for controlling the operation timing of the emission driver 250, and a reset control signal RCS for controlling the operation timing of the reset driver 260. For example, the timing controller 210 may generate the scan control signal SCS, the emission control signal ECS, and the reset control signal RCS, output the scan control signal SCS to the scan driver 230 through a scan control line, output the emission control signal ECS to the emission driver 250 through an emission control line, and output the reset control signal RCS to the reset driver 260 through a reset control line.

The timing controller 210 drives the read-out circuit 300. For example, the timing controller 210 may output a first sampling signal SHS, a second sampling signal SHR, and a feedback reset signal IRST to the read-out circuit 300. The timing controller 210 may control the driving timing of the read-out circuit 300. A method in which the timing controller 210 controls the read-out circuit 300 by outputting the first sampling signal SHS, the second sampling signal SHR, and the feedback reset signal IRST will be described later with reference to FIG. 12.

The timing controller 210 drives the optical sensors PS and the pixels PX of the display panel 10 at the first frame frequency. For example, the timing controller 210 outputs the scan control signal SCS, the data control signal DCS, the emission control signal ECS, and the reset control signal RCS according to the first frame frequency.

The data driver 220 may convert the image data DATA into analog data voltages and output the analog data voltages to data lines DL. The data driver 220 may convert the image data DATA into the analog data voltages.

The scan driver 230 may generate scan write signals according to the scan control signal SCS, and may sequentially output the scan write signals to scan write lines GWL1 to GWLn. For example, the scan driver 230 receives the scan control signal SCS according to the first frame frequency, and outputs the scan write signal according to the first frame frequency.

The power supply unit 240 may generate and supply a first driving voltage to a driving voltage line VL, and may generate and supply a second driving voltage to the driving voltage line VL. The driving voltage line VL may include a first driving voltage line and a second driving voltage line. The first driving voltage may be a high potential voltage for driving a light emitting element and a photoelectric conversion element, and the second driving voltage may be a low potential voltage for driving the light emitting element and the photoelectric conversion element. In other words, the first driving voltage may have a higher potential than the second driving voltage.

The emission driver 250 may generate emission signals according to the emission control signal ECS, and may sequentially output the emission signals to emission lines EML. For example, the emission driver 250 receives the emission control signal ECS according to the first frame frequency, and outputs the emission signals according to the first frame frequency. Although it is illustrated that the emission driver 250 exists separately from the scan driver 230, the present disclosure is not limited thereto and the emission driver 250 may be included in the scan driver 230.

The reset driver 260 may generate reset signals according to the reset control signal RCS, and may sequentially output the reset signals to reset lines RSTL. For example, the reset driver 260 receives the reset control signal RCS according to the first frame frequency, and outputs the reset signals according to the first frame frequency.

The read-out circuit 300 may be connected to each optical sensor PS through a light sensing line FRL, and may receive the light sensing signal (e.g., a current flowing through the optical sensor PS) of each optical sensor PS to produce a pulse wave signal. A user's blood pressure may be calculated based on the pulse wave signal. Further, the read-out circuit 300 may detect a user's fingerprint input. The read-out circuit 300 may be an integrated circuit (IC) and attached on a display circuit board by a chip on film (COF) method, but is not limited thereto, and may be attached on the non-active region NAR of the display panel 10 in a chip on glass (COG) method, a chip on plastic (COP) method or an ultrasonic bonding method.

The read-out circuit 300 may receive the first sampling signal SHS, the second sampling signal SHR, and the feedback reset signal IRST from the timing controller 210. The read-out circuit 300 may turn on a first sampling switch SW1 (see FIG. 11) according to the first sampling signal SHS. The read-out circuit 300 may turn on a second sampling switch SW2 (see FIG. 11) according to the second sampling signal SHR. The read-out circuit 300 may turn on a feedback reset switch SWRO (see FIG. 11) according to the feedback reset signal IRST. Accordingly, the read-out circuit 300 may receive the light sensing signal inputted from the optical sensor PS and generate light sensing data.

The read-out circuit 300 may generate the light sensing data according to the magnitude of the current sensed by each optical sensor PS and transmit the light sensing data to the processor 100, and the processor 100 may produce a user's blood pressure information by analyzing the pressure measurement value measured by the pressure sensing unit PSU and the light sensing data. The display panel 10 further includes the plurality of pixels PX, the plurality of optical sensors PS, the plurality of scan write lines GWL1 to GWLn connected to the plurality of pixels PX and the plurality of optical sensors PS, the plurality of data lines DL and the plurality of emission lines EML connected to the plurality of pixels PX, and the plurality of light sensing lines FRL and the plurality of reset lines RSTL connected to the plurality of optical sensors PS.

The plurality of pixels PX may include a light emitting element and a plurality of transistors for controlling the amount of light emitted from the light emitting element. Each of the plurality of pixels PX may be connected to at least one of the scan write lines GWL1 to GWLn, any one of the data lines DL, at least one of the emission lines EML, and the driving voltage line VL.

The plurality of optical sensors PS may include a photoelectric conversion element and a plurality of transistors for controlling the amount of light received by the photoelectric conversion element. Each of the plurality of optical sensors PS may be connected to any one of the scan write lines GWL1 to GWLn, any one of the reset lines RSTL, any one of the light sensing lines FRL, and the driving voltage line VL.

The plurality of scan write lines GWL1 to GWLn may connect the scan driver 230 to the plurality of pixels PX and the plurality of optical sensors PS. The plurality of scan write lines GWL1 to GWLn may provide the scan write signals outputted from the scan driver 230 to the plurality of pixels PX and the plurality of optical sensors PS.

The plurality of data lines DL may connect the data driver 220 and the plurality of pixels PX. The plurality of data lines DL may provide the image data outputted from the data driver 220 to the plurality of pixels PX.

The plurality of emission lines EML may connect the emission driver 250 and the plurality of pixels PX. The plurality of emission lines EML may provide the emission signal outputted from the emission driver 250 to the plurality of pixels PX.

The plurality of reset lines RSTL may connect the reset driver 260 and the plurality of optical sensors PS. The plurality of reset lines RSTL may provide the reset signal outputted from the reset driver 260 to the plurality of optical sensors PS. The plurality of light sensing lines FRL may connect the plurality of optical sensors PS and the read-out circuit 300. The plurality of light sensing lines FRL may provide photoelectric currents outputted from the plurality of optical sensors PS to the read-out circuit 300. Accordingly, the read-out circuit 300 may generate a user's pulse wave signal or detect a fingerprint.

The plurality of driving voltage lines VL may connect the power supply unit 240 to the plurality of pixels PX and the plurality of optical sensors PS. The plurality of driving voltage lines VL may provide the first driving voltage or the second driving voltage from the power supply unit 240 to the plurality of pixels PX and the optical sensor PS.

Figure 5:
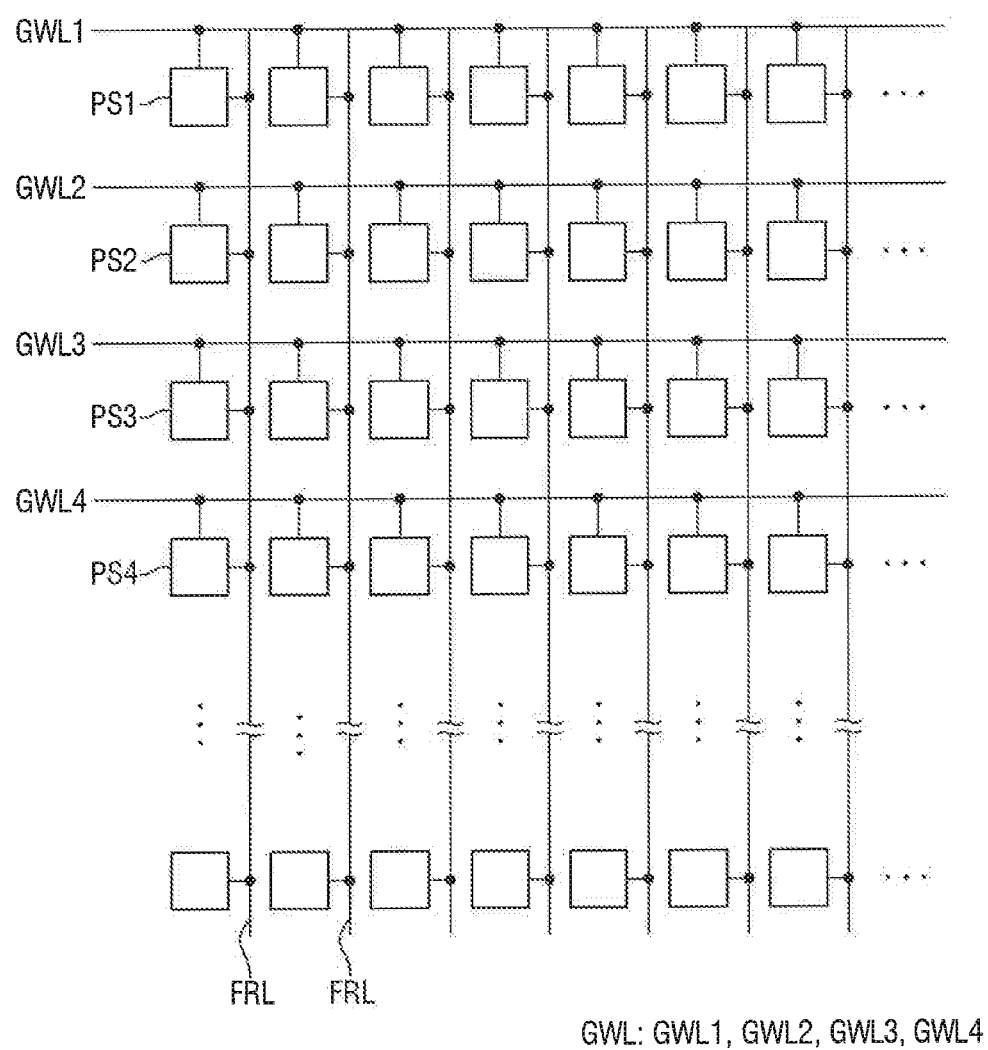
FIG. 5 is a diagram specifically illustrating a connection structure of light sensing pixels and scan write lines of a display panel according to one embodiment of the present disclosure.

FIG. 5 is a diagram specifically illustrating a connection structure of light sensing pixels and scan write lines of a display panel according to one embodiment of the present disclosure.

Referring to FIG. 5, in the active region AAR, red, green, and blue pixels PX and the optical sensors PS are alternately arranged in a matrix form. The optical sensors PS receive the scan write signals through one of the scan write lines GWL. For example, the optical sensors PS of $(4k-3)^{th}$ (k being a natural number) to $4k^{th}$ horizontal lines that are arranged adjacent to each other in the $(4k-3)^{th}$ to $4k^{th}$ horizontal lines are connected to $(4k-3)^{th}$ to $4k^{th}$ scan write lines GWL, respectively.

Hereinafter, for simplicity of description, the $(4k-3)^{th}$ scan write line will be referred to as a first scan write line GWL1, the $(4k-2)^{th}$ scan write line will be referred to as a second scan write line GWL2, the $(4k-1)^{th}$ scan write line will be referred to as a third scan write line GWL3, and the $4k^{th}$ scan write line will be referred to as a fourth scan write line GWL4. Further, the optical sensor connected to the first scan write line GWL1 will be referred to as a first optical sensor PS1, the optical sensor connected to the second scan write line GWL2 will be referred to as a second optical sensor PS2, the optical sensor connected to the third scan write line GWL3 will be referred to as a third optical sensor PS3, and the optical sensor connected to the fourth scan write line GWL4 will be referred to as a fourth optical sensor PS4.

The first to fourth optical sensors PS1 to PS4 transmit light sensing signals LSS (see FIG. 10) according to the amount of light reflected from the front surfaces thereof to the respective light sensing lines FRL in response to first to fourth scan write signals GW1 to GW4, respectively.

Further, the pixels PX receive the scan write signals through two scan write lines GWL among the scan write lines GWL. For example, the pixel PX disposed between the $(4k-3)^{th}$ horizontal line and the $(4k-2)^{th}$ horizontal line is connected to the $(4k-3)^{th}$ and $(4k-2)^{th}$ scan write lines GWL. Further, the pixel PX disposed between the $(4k-2)^{th}$ horizontal line and the $(4k-1)^{th}$ horizontal line is connected to the $(4k-2)^{th}$ and $(4k-1)^{th}$ scan write lines GWL. Further, the pixel PX disposed between the $(4k-1)^{th}$ horizontal line and the $4k^{th}$ horizontal line is connected to the $(4k-1)^{th}$ and $4k^{th}$ scan write lines GWL. This will be described later with reference to FIG. 5.

Hereinafter, for simplicity of description, the pixel connected to the $(4k-2)^{th}$ and $(4k-1)^{th}$ scan write lines GWL will be referred to as a first pixel PX1. In other words, the pixel connected to the first scan write line GWL1 and the second scan write line GWL2 will be referred to as the first pixel PX1. Further, the pixel connected to the $(4k-1)^{th}$ and $4k^{th}$ scan write lines GWL will be referred to as a second pixel PX2. In other words, the pixel connected to the third scan write line GWL3 and the fourth scan write line GWL4 will be referred to as the second pixel PX2.

In summary, the pixels PX and the optical sensors PS are arranged in a matrix form. Among them, the first optical sensor PS1 may be connected to the first scan write line GWL1, the second optical sensor PS2 may be connected to the second scan write line GWL2, the third optical sensor PS3 may be connected to the third scan write line GWL3, and the fourth optical sensor PS4 may be connected to the fourth scan write line GWL4. The first to fourth optical sensors PS1 to PS4 may be repeatedly arranged.

Figure 6:
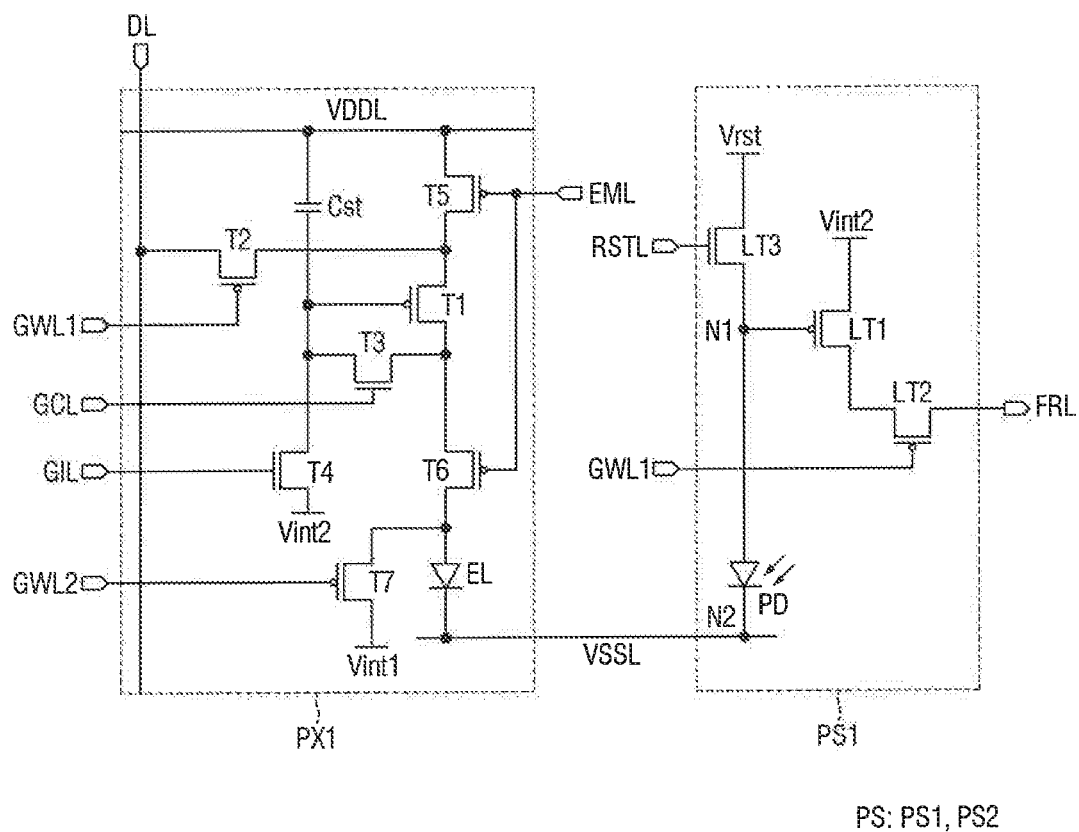
FIG. 6 is a detailed circuit diagram illustrating a pixel and an optical sensor according to one embodiment of the present disclosure.
Figure 7:
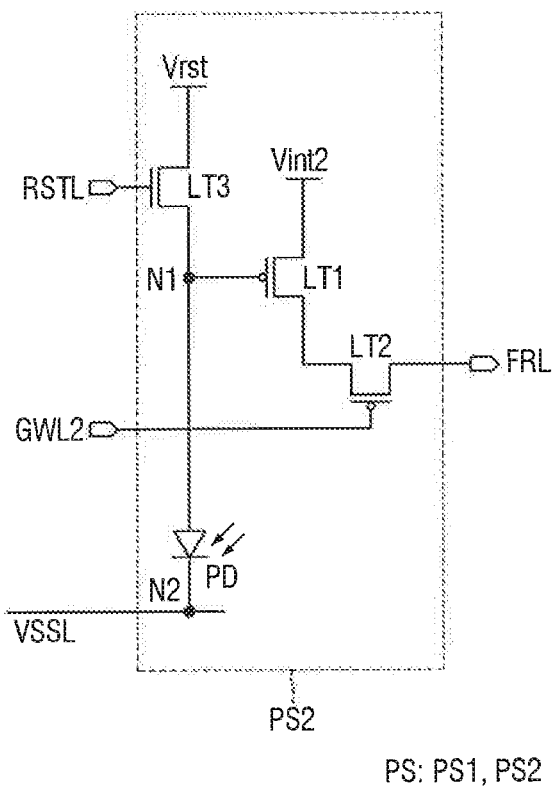
FIG. 7 is a circuit diagram specifically illustrating an optical sensor according to one embodiment of the present disclosure.

FIG. 6 is a detailed circuit diagram illustrating a pixel and an optical sensor according to one embodiment of the present disclosure. FIG. 7 is a circuit diagram specifically illustrating an optical sensor according to one embodiment of the present disclosure.

Referring to FIG. 6, the first pixel PX1 may be connected to a scan start line GIL, a scan control line GCL, the first scan write line GWL1, the second scan write line GWL2, the emission line EML, and the data line DL. Further, each pixel PX may be connected to a first driving voltage line VDDL to which a first driving voltage is applied, a second driving voltage line VSSL to which a second driving voltage is applied, a first initialization voltage line to which a first initialization voltage Vint1 is applied, and a second initialization voltage line to which a second initialization voltage Vint2 is applied.

The first optical sensor PS1 may be connected to the first scan write line GWL1, the reset line RSTL, and the light sensing line FRL. Further, each optical sensor PS may be connected to the second driving voltage line VSSL to which the second driving voltage is applied, a reset voltage line to which a reset voltage Vrst is applied, and the second initialization voltage line to which the second initialization voltage Vint2 is applied.

The first pixel PX1 may include a plurality of transistors, a light emitting element EL, and at least one capacitor Cst. The plurality of transistors may include first to seventh transistors T1, T2, T3, T4, T5, T6, and T7. Among them, the first transistor T1 may be a driving transistor, and the second to seventh transistors T2 to T7 may be transistors serving as switch elements that are turned on or off in response to scan write signals applied to gate electrodes thereof.

The first transistor T1 may include a gate electrode, a first electrode, and a second electrode. The first transistor T1 may control a source-drain current Isd (hereinafter, referred to as "driving current Isd") according to the data voltage applied to the gate electrode thereof. The driving current Isd flowing through a channel of the first transistor T1 is proportional to the square of a difference between a source-gate voltage (a voltage between the source electrode and the gate electrode of the first transistor T1) and an absolute value of a threshold voltage Vth, as shown in Eq. (1).

$$Isd = k' \times (Vsg - |Vth|)^2 \qquad (1)$$

In Eq. (1), k' denotes a proportional coefficient determined by the structure and physical characteristics of the first transistor T1, Vsg denotes the source-gate voltage of the first transistor T1, and Vth represents the threshold voltage of the first transistor T1.

The gate electrode of the first transistor T1 may be connected to a first electrode of the third transistor T3 and one electrode of the capacitor Cst, the first electrode of the first transistor T1 may be connected to a second electrode of the second transistor T2 and a second electrode of the fifth transistor T5, and the second electrode of the first transistor T1 may be connected to a second electrode of the third transistor T3 and a first electrode of the sixth transistor T6.

The light emitting element EL emits light by the driving current Isd. A light emission amount of the light emitting element EL may be proportional to the driving current Isd.

The light emitting element EL may be an organic light emitting diode including an anode electrode, a cathode electrode, and an organic light emitting layer disposed between the anode electrode and the cathode electrode. Alternatively, the light emitting element EL may be an inorganic light emitting diode including an anode electrode, a cathode electrode, and an inorganic light emitting layer disposed between the anode electrode and the cathode electrode, or may be a quantum dot light emitting element EL including a quantum dot light emitting layer disposed between the anode electrode and the cathode electrode. Further, the light emitting element EL may be a micro light emitting diode.

The anode electrode of the light emitting element EL may be connected to the second electrode of the sixth transistor T6 and the second electrode of the seventh transistor T7, and the cathode electrode may be connected to the second driving voltage line VSSL.

The second transistor T2 may be turned on by the scan write signal of the first scan write line GWL1 to connect the first electrode of the first transistor T1 to the data line DL A gate electrode of the second transistor T2 may be connected to the first scan write line GWL1, a first electrode of the second transistor T2 may be connected to the data line DL, and the second electrode of the second transistor T2 may be connected to the first electrode of the first transistor T1.

The third transistor T3 may be turned on by the scan write signal of the scan control line GCL to connect the gate electrode and the second electrode of the first transistor T1. In other words, when the third transistor T3 is turned on, the gate electrode and the second electrode of the first transistor T1 are connected and, thus, the first transistor T1 may be driven as a diode. A gate electrode of the third transistor T3 may be connected to the scan control line GCL, the second electrode thereof may be connected to the second electrode of the first transistor T1, and the first electrode thereof may be connected to the gate electrode of the first transistor T1.

The fourth transistor T4 may be turned on by the scan write signal of the scan start line GIL to connect the second initialization voltage line and the gate electrode of the first transistor T1. In this case, the gate electrode of the first transistor T1 may be discharged to the second initialization voltage Vint2 of the second initialization voltage line. A gate electrode of the fourth transistor T4 may be connected to the scan start line GIL, and a first electrode and a second electrode of the fourth transistor T4 may be connected to the second initialization voltage line and the gate electrode of the first transistor T1, respectively.

The fifth transistor T5 may be turned on by an emission signal of the emission line EML to connect the first electrode of the first transistor T1 to the first driving voltage line VDDL. A gate electrode of the fifth transistor T5 may be connected to the emission line EML, a first electrode thereof may be connected to the first driving voltage line VDDL, and the second electrode thereof may be connected to the first electrode of the first transistor T1.

The sixth transistor T6 may be turned on by the emission signal of the emission line EML to connect the second electrode of the first transistor T1 to the anode electrode of the light emitting element EL. The gate electrode of the sixth transistor T6 may be connected to the emission line EML, the first electrode thereof may be connected to the second electrode of the first transistor T1, and the second electrode thereof may be connected to the anode electrode of the light emitting element EL.

When both the fifth transistor T5 and the sixth transistor T6 are turned on, the driving current Isd may be supplied to the light emitting element EL.

The seventh transistor T7 may be turned on by the scan write signal of the second scan write line GWL2 to connect the first initialization voltage line to the anode electrode of the light emitting element EL. In this case, the anode electrode of the light emitting element EL may be discharged to the first initialization voltage Vint1. A gate electrode of the seventh transistor T7 may be connected to the second scan write line GWL2, a first electrode of the seventh transistor T7 may be connected to the first initialization voltage line, and the second electrode of the seventh transistor T7 may be connected to the anode electrode of the light emitting element EL.

The capacitor Cst may be formed between the gate electrode of the first transistor T1 and the first driving voltage line VDDL One electrode of the capacitor Cst may be connected to the gate electrode of the first transistor T1, and the other electrode of the capacitor Cst may be connected to the first driving voltage line VDDL. Accordingly, the capacitor Cst may maintain a potential difference between the gate electrode of the first transistor T1 and the first driving voltage line VDDL.

The second pixel PX2 may be connected to the scan start line GIL, the scan control line GCL, the third scan write line GWL3, the fourth scan write line GWL4, the emission line EML, and the data line DL.

The second transistor T2 of the second pixel PX2 may be turned on by the scan write signal of the third scan write line GWL3 to connect the first electrode of the first transistor T1 to the data line DL. A gate electrode of the second transistor T2 may be connected to the third scan write line GWL3, a first electrode of the second transistor T2 may be connected to the data line DL, and the second electrode of the second transistor T2 may be connected to the first electrode of the first transistor T1. Further, the seventh transistor T7 of the second pixel PX2 may be turned on by the scan write signal of the fourth scan write line GWL4 to connect the first initialization voltage line to the anode electrode of the light emitting element EL. The description of the second pixel PX2 is substantially the same as the description of the first pixel PX1 except that the first pixel PX1 is connected to the first scan write line GWL1 and the second scan write line GWL2, whereas the second pixel PX2 is connected to the third scan write line GWL3 and the fourth scan write line GWL4, and thus will be omitted.

Each optical sensor PS includes the first optical sensor PS1 connected to the first scan write line GWL1, the second optical sensor PS2 connected to the second scan write line GWL2, the third optical sensor PS3 connected to the third scan write line GWL3, and the fourth optical sensor PS4 connected to the fourth scan write line GWL4. The first to fourth optical sensors PS1 to PS4 may be repeatedly arranged along a plurality of rows in the display panel 10.

The first optical sensor PS1 may include a plurality of sensing transistors and a photoelectric conversion element PD. The plurality of sensing transistors may include first to third sensing transistors LT1, LT2, and LT3. The first optical sensor PS1 may include a first node N1 between the first sensing transistor LT1, the third sensing transistor LT3, and the photoelectric conversion element PD, and a second node N2 between the second driving voltage line VSSL and the photoelectric conversion element PD. The first sensing transistor LT1 may be a driving transistor, and the second and third sensing transistors LT2 and LT3 may be transistors serving as switch elements that are turned on or turned off according to the scan write signal and the reset signal applied to the gate electrodes thereof.

When the plurality of light emitting elements EL and the plurality of photoelectric conversion elements PD are disposed on one display panel 10, a signal line or a voltage line for driving the light emitting element EL may be shared in driving the photoelectric conversion elements PD. In other words, by minimizing additional signal lines or voltage lines for driving the plurality of photoelectric conversion elements PDs on the display panel 10, the resolution of the display panel 10 can be ensured and the bezel area can be minimized. For example, the signal line connected to the gate electrode of the second transistor T2 of the pixel PX may be shared with the signal line connected to the gate electrode of the second sensing transistor LT2 of the optical sensor PS. In other words, the gate electrode of the second transistor T2 of the first pixel PX1 and the gate electrode of the second sensing transistor LT2 may be connected to the first scan write line GWL1. As another example, the second driving voltage line VSSL may be a common voltage line connected to the cathode electrode of the light emitting element EL and the cathode electrode of the photoelectric conversion element PD. As yet another example, the second initialization voltage line to which the second initialization voltage Vint2 is applied may be a common voltage line connected to the first electrode of the fourth transistor T4 of the first pixel PX1 and the first electrode of the first sensing transistor LT1 of the optical sensor PS.

Each of the photoelectric conversion elements PD may be a light receiving diode including an anode electrode, a cathode electrode, and a photoelectric conversion layer disposed between the anode electrode and the cathode electrode. Each of the photoelectric conversion elements PD may convert externally incident light into an electrical signal. The photoelectric conversion element PD may be a light receiving diode or a phototransistor formed of a pn-type or pin-type inorganic material. Alternatively, the photoelectric conversion element PD may also be an organic light receiving diode including an electron donating material generating donor ions and an electron accepting material generating acceptor ions.

The anode electrode of the photoelectric conversion element PD may be connected to the first node N1, and the cathode electrode thereof may be connected to the second node N2.

When the photoelectric conversion element PD is exposed to external light, photocharges may be generated, and the generated photocharges may be accumulated in the anode electrode of the photoelectric conversion element PD. In this case, the voltage of the first node N1 electrically connected to the anode electrode of the photoelectric conversion element PD may increase. When the photoelectric conversion element PD and the light sensing line FRL are connected by the turn-on of the first and second sensing transistors LT1 and LT2, a current may flow in the light sensing line FRL in proportion to the voltage of the first node N1 in which charges are accumulated.

The first sensing transistor LT1 may be turned on by the voltage of the first node N1 applied to the gate electrode thereof to connect the second initialization voltage line and the second electrode of the second sensing transistor LT2. In this case, the second electrode of the second sensing transistor LT2 may be discharged to the second initialization voltage Vint2. The gate electrode of the first sensing transistor LT1 may be connected to the first node N1, the first electrode thereof may be connected to the second initialization voltage line, and the second electrode thereof may be connected to the first electrode of the second sensing transistor LT2. The first sensing transistor LT1 may be a source follower amplifier that generates a source-drain current in proportion to the amount of electric charges of the first node N1 inputted to the gate electrode thereof. The first electrode of the first sensing transistor LT1 may be connected to the first driving voltage line VDDL or the first initialization voltage line.

The second sensing transistor LT2 may be turned on by the scan write signal of the first scan write line GWL1 to connect the second electrode of the first sensing transistor LT1 and the light sensing line FRL. The light sensing line FRL may transmit the light sensing signal to the read-out circuit 300 (see FIG. 2). The gate electrode of the second sensing transistor LT2 may be connected to the first scan write line GWL1, the first electrode thereof may be connected to the second electrode of the first sensing transistor LT1, and the second electrode thereof may be connected to the light sensing line FRL.

The third sensing transistor LT3 may be turned on by the reset signal of the reset line RSTL to reset the first node N1 to the reset voltage Vrst. The gate electrode of the third sensing transistor LT3 may be connected to the reset line RSTL, the first electrode thereof may be connected to the reset voltage line, and the second electrode thereof may be connected to the first node N1. When the reset driver for outputting the reset signal of the reset line RSTL is omitted, the third sensing transistor LT3 may be turned on by the scan write signal.

Referring further to FIG. 7, the second optical sensor PS2 may include the plurality of sensing transistors and the photoelectric conversion element PD. The plurality of sensing transistors may include the first to third sensing transistors LT1 to LT3. The second optical sensor PS2 may include the first node N1 between the first sensing transistor LT1, the third sensing transistor LT3, and the photoelectric conversion element PD, and the second node N2 between the second driving voltage line VSSL and the photoelectric conversion element PD. The first sensing transistor LT1 may be a driving transistor, and the second and third sensing transistors LT2 and LT3 may be transistors serving as switch elements that are turned on or turned off according to the scan write signal and the reset signal applied to the gate electrodes thereof.

The second sensing transistor LT2 of the second optical sensor PS2 may be turned on by the scan write signal of the second scan write line GWL2 to connect the second electrode of the first sensing transistor LT1 and the light sensing line FRL. The light sensing line FRL may transmit the light sensing signal to the read-out circuit 300 (see FIG. 2). The gate electrode of the second sensing transistor LT2 may be connected to the second scan write line GWL2, the first electrode thereof may be connected to the second electrode of the first sensing transistor LT1, and the second electrode thereof may be connected to the light sensing line FRL. Since the second optical sensor PS2 is substantially the same as the first optical sensor PS1 except that it is connected to the second scan write line GWL2, whereas the first optical sensor PS1 is connected to the first scan write line GWL1, the description thereof will be omitted.

Further, the second sensing transistor LT2 of the third optical sensor PS3 may be turned on by the scan write signal of the third scan write line GWL3 to connect the second electrode of the first sensing transistor LT1 and the light sensing line FRL. Further, the second sensing transistor LT2 of the fourth optical sensor PS4 may be turned on by the scan write signal of the fourth scan write line GWL4 to connect the second electrode of the first sensing transistor LT1 and the light sensing line FRL. The description of the third optical sensor PS3 and the fourth optical sensor PS4 is substantially the same as the description of the second optical sensor PS2 except for the third scan write line GWL3 and the fourth scan write line GWL4, and thus will be omitted.

When the first electrodes of the first to seventh transistors T1 to T7 and the first to third sensing transistors LT1 to LT3 are source electrodes, the second electrodes thereof may be drain electrodes. Alternatively, when the first electrodes of the first to seventh transistors T1 to T7 and the first to third sensing transistors LT1 to LT3 are drain electrodes, the second electrodes thereof may be source electrodes.

The active layers of the first to seventh transistors T1 to T7, and the first to third sensing transistors LT1 to LT3 may be made of any one of polysilicon, amorphous silicon, and an oxide semiconductor.

For example, the first and second transistors T1 and T2, the fifth to seventh transistors T5 to T7, and the first and second sensing transistors LT1 and LT2 may be P-type transistors. In this case, the active layers of the first and second transistors T1 and T2, the fifth to seventh transistors T5 to T7, and the first and second sensing transistors LT1 and LT2 may be made of polysilicon. Further, each of the third transistor T3, the fourth transistor T4, and the third sensing transistor LT3 may be an N-type transistor forming the active layer made of an oxide semiconductor.

However, embodiments are not limited thereto, and each of the first to seventh transistors T1 to T7, and the first to third sensing transistors LT1 to LT3 may be a P-type transistor. As another example, the first to third sensing transistors LT1 to LT3 may be formed of P-type transistors. In this case, the timing diagrams of FIGS. 8 and 9 should be modified to suit the characteristics of each transistor.

Figure 8:
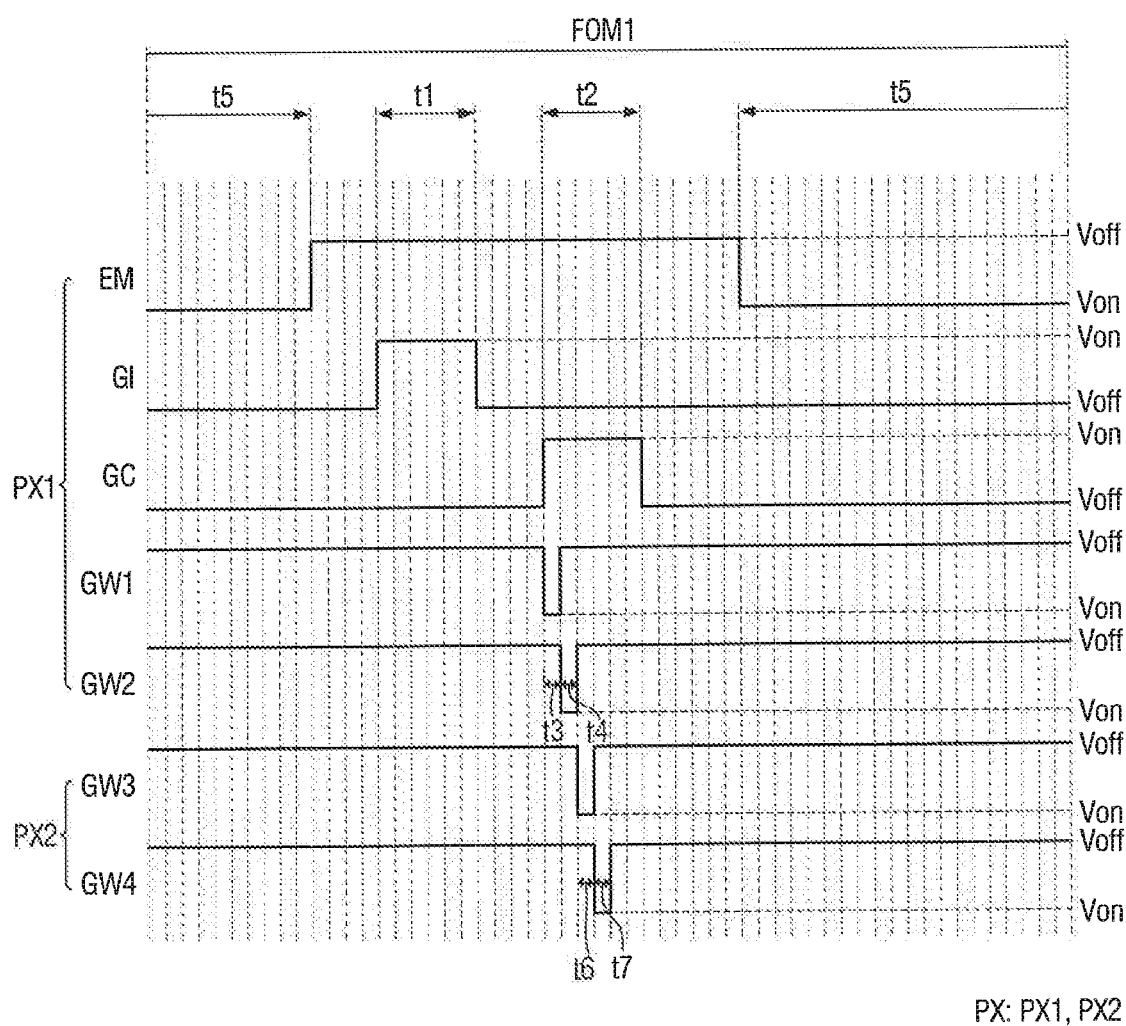
FIG. 8 is a timing diagram illustrating the operation of the pixel shown in FIGS. 6 and 7.

FIG. 8 is a timing diagram illustrating the operation of the pixel shown in FIGS. 6 and 7.

Referring to FIGS. 6 to 8, the emission signal EM, which is a signal applied to the emission line EML, is a signal for controlling turn-on and turn-off of the fifth transistor T5 and the sixth transistor T6. The scan start signal GI, which is a signal applied to the scan start line GIL, is a signal for controlling turn-on and turn-off of the fourth transistor T4. The scan control signal GC, which is a signal applied to the scan control line GCL, is a signal for controlling turn-on and turn-off of the third transistor T3.

The first scan write signal GW1, which is a signal applied to the first scan write line GWL1 of the first pixel PX1, is a signal for controlling turn-on and turn-off of the second sensing transistor LT2 of the first optical sensor PS1 and the second transistor T2 of the first pixel PX1. The second scan write signal GW2, which is a signal applied to the second scan write line GWL2 of the first pixel PX1, is a signal for controlling turn-on and turn-off of the second sensing transistor LT2 of the second optical sensor PS2 and the seventh transistor T7. The third scan write signal GW3, which is a signal applied to the third scan write line GWL3, is a signal for controlling turn-on and turn-off of the third optical sensor PS3 of the second sensing transistor LT2 and the second transistor T2 of the second pixel PX2. The fourth scan write signal GW4, which is a signal applied to the fourth scan write line GWL4, is a signal for controlling turn-on and turn-off of the fourth optical sensor PS4 and the seventh transistor T7 of the second pixel PX2.

The emission signal EM, the scan start signal GI, the scan control signal GC, and the first to fourth scan write signals GW1 to GW4 may have a signal repeated at a cycle of one frame period. For example, one frame period in which the display panel 10 is driven may correspond to the first frame period FMO1 having the first frame frequency.

The first frame period FMO1 may be divided, according to the operation of the pixel PX, into a first period t1 for initializing the voltage of the gate electrode of the first transistor T1 to the second initialization voltage Vint2, a second period t2 for supplying a data voltage to the first electrode of the first transistor T1 and sampling the threshold voltage of the first transistor T1, a third period t3 for supplying a data voltage to the first electrode of the first transistor T1 and sampling the threshold voltage of the first transistor T1, a fourth period t4 for initializing the voltage of the anode electrode of the light emitting element EL to the first initialization voltage Vint1, and a fifth period t5 for allowing the light emitting element EL to emit light.

The scan start signal GI may have a gate-on voltage Von during the first period t1, and may have a gate-off voltage Voff during the remaining periods. In other words, the scan start signal GI may have the gate-off voltage Voff in the second to fifth periods t2-t5. The scan control signal GC may have the gate-on voltage Von during the second period t2, and may have the gate-off voltage Voff during the remaining periods. The first scan write signal GW1 may have the gate-on voltage Von during the third period t3, and may have the gate-off voltage Voff during the remaining periods. The third period t3 may overlap the second period t2. The second scan write signal GW2 may have the gate-on voltage Von during the fourth period t4, and may have the gate-off voltage Voff during the remaining periods. The fourth period t4 may overlap the second period t2. The third scan write signal GW3 may have the gate-on voltage Von during a sixth period t6, and may have the gate-off voltage Voff during the remaining periods. The sixth period t6 may overlap the second period t2. The fourth scan write signal GW4 may have the gate-on voltage Von during the seventh period t7, and may have the gate-off voltage Voff during the remaining periods. The seventh period t7 may overlap the second period t2. The emission signal EM may have the gate-on voltage Von during the fifth period t5, and may have the gate-off voltage Voff during the remaining periods.

The gate-on voltage Von of the scan start signal GI and the scan control signal GC may be a gate high voltage, and the gate-off voltage Voff thereof may be a gate low voltage. The gate-on voltage Von of the first to fourth scan write signals GW1 to GW4 and the emission signal EM may be the gate low voltage, and the gate-off voltage Voff thereof may be the gate high voltage.

Hereinafter, the operation of the first pixel PX1 will be described.

The scan start signal GI having the gate-on voltage Von is supplied to the scan start line GIL during the first period t1. During the first period t1, the fourth transistor T4 is turned on by the scan start signal GI. Due to the turn-on of the fourth transistor T4, the gate electrode of the first transistor T1 is initialized to the second initialization voltage Vint2 of the second initialization voltage line.

Then, the scan control signal GC having the gate-on voltage Von is supplied to the scan control line GCL during the second period t2. Accordingly, the third transistor T3 connected to the scan control line GCL is turned on to connect the gate electrode and the second electrode of the first transistor T1, and thus, the first transistor T1 operates as a diode.

During the third period t3, the first scan write signal GW1 having the gate-on voltage Von is supplied to the first scan write line GWL1. Accordingly, the second transistor T2 connected to the first scan write line GWL1 is turned on, and a data voltage (hereinafter, referred to as "Vdata") is applied to the first electrode of the first transistor T1. At this time, the voltage (Vsg=Vdata−Vint2) between the first electrode and the gate electrode of the first transistor T1 is smaller than the absolute value of the threshold voltage Vth of the first transistor T1, so that a current path is formed until the voltage Vsg between the gate electrode and the source electrode of the first transistor T1 reaches the absolute value of the threshold voltage Vth. Accordingly, the voltage of the gate electrode and the first electrode of the first transistor T1 rises up to the difference voltage (Vdata−|Vth|) between the data voltage and the absolute value of the threshold voltage of the first transistor T1 during the second period t2. In this case, "Vdata−|Vth|" may be held in the capacitor Cst.

Since the first transistor T1 is a P-type transistor, the driving current Isd of the first transistor T1 may be proportional to a voltage Vsd between the source electrode and the drain electrode of the first transistor T1 in a section in which the voltage Vsd between the source electrode and the drain electrode of the first transistor T1 is greater than 0V. In addition, the threshold voltage Vth of the first transistor T1 may be less than 0V.

During the fourth period t4, the second scan write signal GW2 having the gate-on voltage Von is supplied to the second scan write line GWL2. Accordingly, the seventh transistor T7 connected to the second scan write line GWL2 is turned on. Accordingly, the anode electrode of the light emitting element EL is initialized to the first initialization voltage Vint1 of the first initialization voltage line. The fourth period t4 may occur immediately after the third period t3.

Then, the emission signal EM having the gate-on voltage Von is supplied to the emission line EML during the fifth period t5. During the fifth period t5, each of the fifth transistor T5 and the sixth transistor T6 is turned on by the emission signal EM. The first electrode of the first transistor T1 is connected to the first driving voltage line VDDL due to the turn-on of the fifth transistor T5, and the second electrode of the first transistor T1 is connected to the anode electrode of the light emitting element EL due to the turn-on of the sixth transistor T6.

When the fifth transistor T5 and the sixth transistor T6 are turned on, the driving current Isd flowing according to the voltage of the gate electrode of the first transistor T1 may be supplied to the light emitting element EL. The driving current Isd may be defined as in Eq. (2).

$$Isd = K' \times (ELVDD - (Vdata - |Vth|) - |Vth|)^2 \qquad (2)$$

In Eq. (2), k' represents a proportional coefficient determined by the structure and physical characteristics of the first transistor T1, Vth represents the threshold voltage of the first transistor T1, ELVDD represents the first driving voltage ELVDD of the first driving voltage line VDDL, and "Vdata" represents the data voltage. The gate voltage of the first transistor T1 is "Vdata−|Vth|," and the voltage of the first electrode is "ELVDD." When Eq. (2) is summarized, Eq. (3) is derived.

$$Isd = K' \times (ELVDD - Vdata)^2 \qquad (3)$$

Consequently, as illustrated in Equation 3, the driving current Isd does not depend on the threshold voltage Vth of the first transistor T1. In other words, the threshold voltage Vth of the first transistor T1, which is the driving transistor, is compensated, and the light emitting element EL may emit light according to the magnitude of the driving current Isd controlled by the first driving voltage ELVDD and the data voltage.

The operation of the second pixel PX2 is substantially the same as that of the first pixel PX1 except that the third scan write signal GW3 and the fourth scan write signal GW4 are supplied.

Also in the case of the second pixel PX2, the third scan write signal GW3 having the gate-on voltage Von is supplied to the third scan write line GWL3 during the sixth period t6. Accordingly, the second transistor T2 connected to the first scan write line GWL1 is turned on, and the data voltage (hereinafter, referred to as "Vdata") is supplied to the first electrode of the first transistor T1. Further, during the seventh period t7, the fourth scan write signal GW4 having the gate-on voltage Von is supplied to the fourth scan write line GWL4. Accordingly, the seventh transistor T7 connected to the fourth scan write line GWL4 is turned on. Accordingly, the anode electrode of the light emitting element EL is initialized to the first initialization voltage Vint1 of the first initialization voltage line. The seventh period t7 may occur immediately after the sixth period t6. The operation of the second pixel PX2 is substantially the same as the operation of the first pixel PX1 except that the third scan write signal GW3 and the fourth scan write signal GW4 are supplied, so that the description thereof will be omitted.

Figure 9:
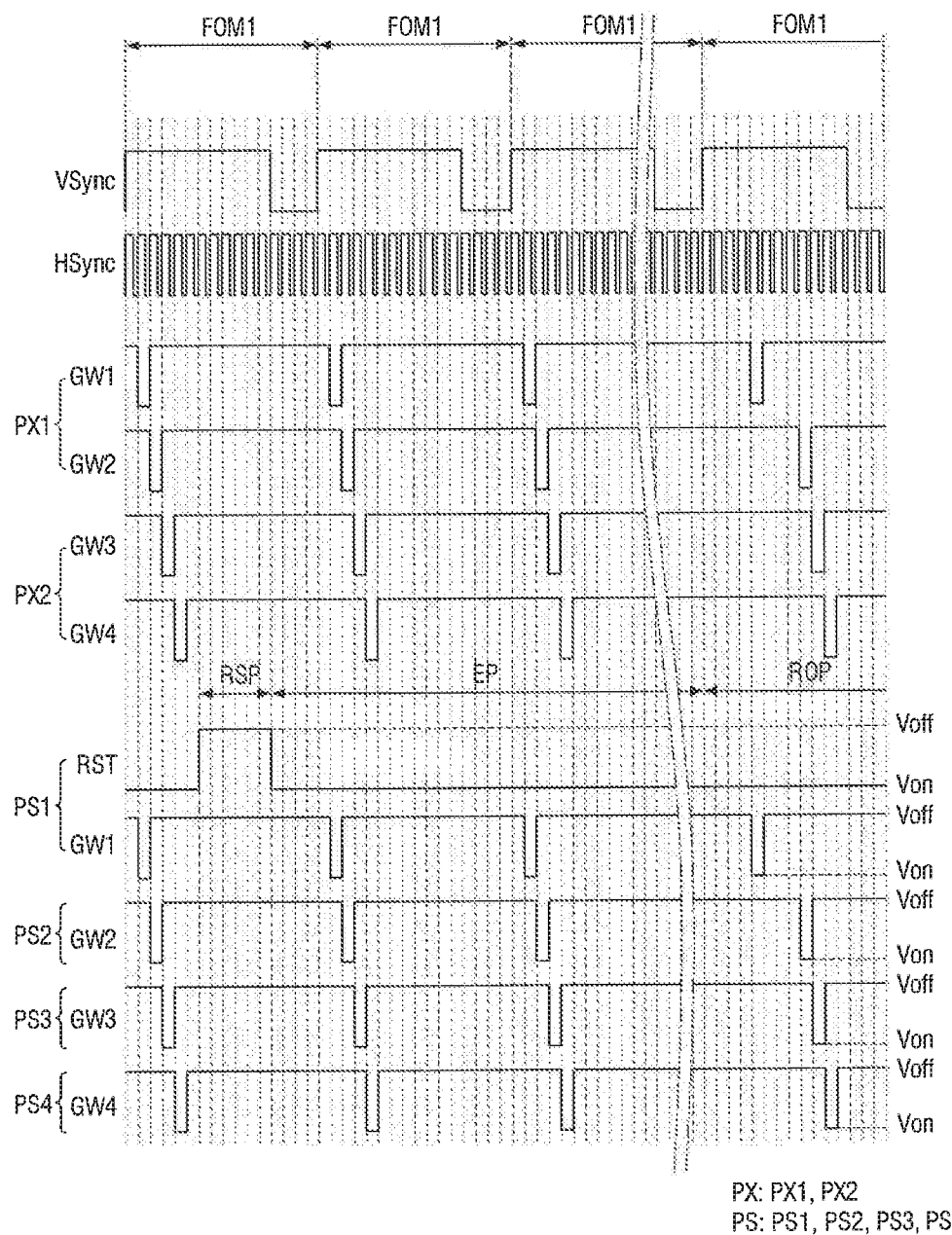
FIG. 9 is a timing diagram illustrating the operation of the optical sensor and the pixel and shown in FIGS. 6 and 7.

FIG. 9 is a timing diagram illustrating the operation of the optical sensor and the pixel and shown in FIGS. 6 and 7.

Hereinafter, the operations of the scan write signal GW and the reset signal RST for controlling the optical sensor PS will be described with reference to FIGS. 6, 7 and 9.

First, the first scan write signal GW1 is a signal applied to the first scan write line GWL1 as described above. The first scan write signal GW1 is a signal for controlling turn-on and turn-off of the second sensing transistor LT2 and the second transistor T2 of the first optical sensor PS1. The second scan write signal GW2 is a signal applied to the second scan write line GWL2. The second scan write signal GW2 is a signal for controlling turn-on and turn-off of the second sensing transistor LT2 and the second transistor T2 of the second optical sensor PS2. The third scan write signal GW3 is a signal applied to the third scan write line GWL3. The third scan write signal GW3 is a signal for controlling turn-on and turn-off of the second sensing transistor LT2 and the second transistor T2 of the third optical sensor PS3. The fourth scan write signal GW4 is a signal applied to the fourth scan write line GWL4. The fourth scan write signal GW4 is a signal for controlling turn-on and turn-off of the second sensing transistor LT2 and the second transistor T2 of the fourth optical sensor PS4.

The reset signal RST of the optical sensor PS, which is a signal applied to the reset line RSTL, is a signal for controlling turn-on and turn-off of the third sensing transistor LT3. The reset signal RST may be a separate signal different from the scan write signals. In other words, the reset timing of the optical sensor PS and the number of times of resetting the optical sensor PS may be independently adjusted by separating the reset signal RST of the optical sensor PS from the scan write signals of the pixel PX without sharing them. For example, the reset signal RST may be outputted when a user's touch occurs so that the optical sensor PS may enter a reset period RSP.

One frame period of the optical sensor PS may be divided into the reset period RSP for resetting the anode electrode of the photoelectric conversion element PD to the reset voltage Vrst, a light exposure period EP for exposing the photoelectric conversion element PD to external light and generating photocharges according to the intensity of the external light so that the voltage of the anode electrode of the photoelectric conversion element PD and the voltage of the first node N1 increase, and a light sensing period ROP for turning on the second sensing transistor LT2 and reading light according to the magnitude of the current flowing through the light sensing line FRL.

The reset signal RST may have the gate-on voltage Von during the reset period RSP and the gate-off voltage Voff during the remaining periods. In other words, the reset signal RST may have the gate-off voltage Voff during the light exposure period EP and the light sensing period ROP. The gate-on voltage Von of the reset signal RST may be the gate high voltage, and the gate-off voltage Voff of the reset signal RST may be the gate low voltage.

The reset period RSP may be started according to the request of the processor 100. During the reset period RSP, the reset signal RST having the gate-on voltage Von is supplied to the reset line RSTL. Accordingly, the third sensing transistor LT3 is turned on, and the anode electrode of the photoelectric conversion element PD and the first node N1 are reset to the reset voltage Vrst. The second driving voltage corresponding to a voltage higher than the reset voltage Vrst is applied to the second node N2 and the cathode electrode of the photoelectric conversion element PD, so that the photoelectric conversion element PD maintains a reverse bias state. For example, the voltage level of the first node N1 may be about −6.5V, and the voltage level of the second node N2 may be about −2.5V.

Thereafter, during the light exposure period EP, the photoelectric conversion element PD may be exposed to the external light emitted from the light emitting element EL. When a user's touch occurs, the photoelectric conversion element PD may generate photocharges corresponding to the light reflected from the user, and a reverse current may be generated in proportion to the amount of the generated photocharges. In other words, a current flowing from the second node N2 to the first node N1 may be generated. Accordingly, the voltage of the first node N1 may increase. The voltage of the first node N1 may increase until the voltage (Vsg=Vint2−Vg) between the gate electrode and the first electrode of the first sensing transistor LT1 reaches the absolute value of the threshold voltage Vth of the first sensing transistor LT1. When the first node N1 reaches the threshold voltage Vth of the first sensing transistor LT1, the first sensing transistor LT1 may be turned on. Since the light sensing signal increases as the amount of electric charges charged in the first node N1 increases, the light exposure period EP may be set to be sufficiently long.

Then, during the light sensing period ROP, the first to fourth scan write signals GW1 to GW4 having the gate-on voltage Von are sequentially supplied to the first to fourth scan write lines GWL1 to GWL4. Accordingly, the second sensing transistors LT2 of the optical sensors PS are turned on, and the light sensing signal corresponding to the current flowing through the first sensing transistor LT1 may be outputted to the light sensing line FRL. The current flowing through the first sensing transistor LT1 is a source-drain current generated in proportion to the amount of electric charges of the first node N1 inputted to the gate electrode of the first sensing transistor LT1. Accordingly, a change in the voltage of the first node N1 may be sensed. A process in which the read-out circuit 300 connected to the light sensing line FRL detects a sensing signal voltage VC during the light sensing period ROP will be described with reference to FIGS. 9 and 10.

Figure 10:
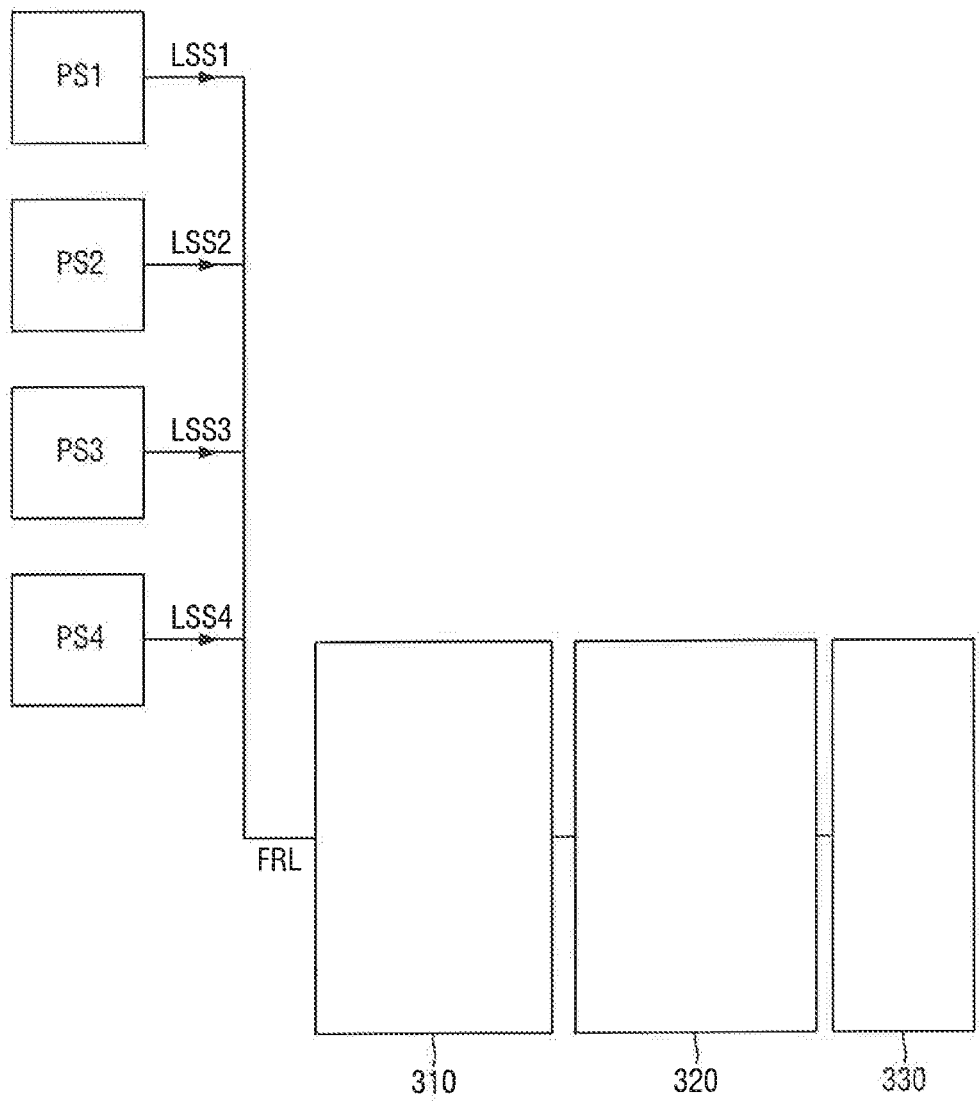
FIG. 10 is a block diagram illustrating first to fourth optical sensors and a read-out circuit.
Figure 11:
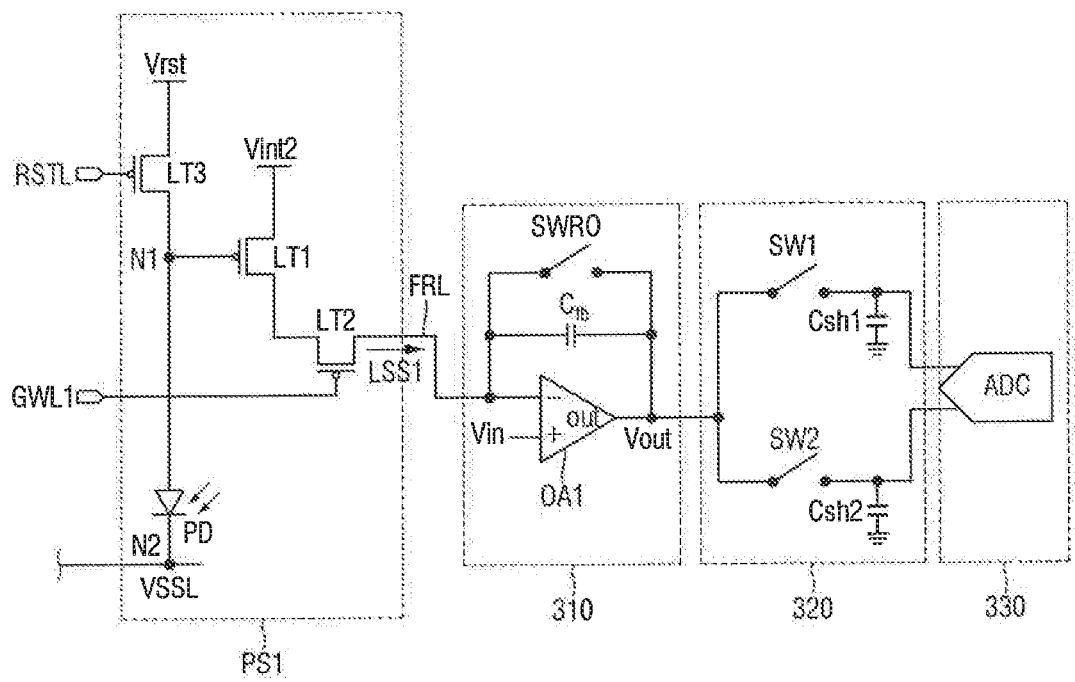
FIG. 11 is a circuit diagram specifically illustrating a first optical sensor and a read-out circuit.
Figure 12:
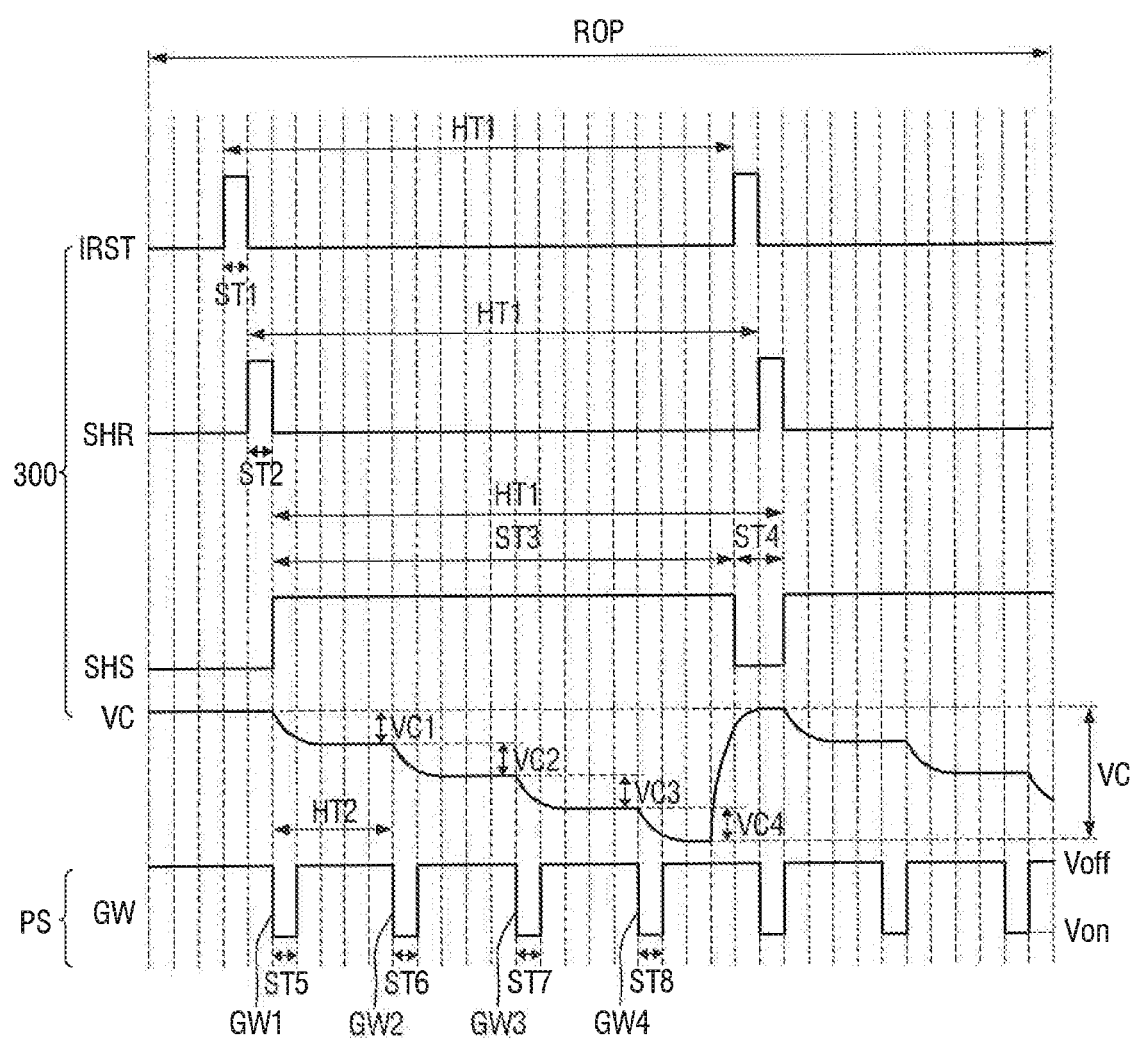
FIG. 12 is a waveform diagram illustrating a scan write signal and signals of the read-out circuit of FIG. 10 according to a light sensing period.

FIG. 10 is a block diagram illustrating first to fourth optical sensors and a read-out circuit. FIG. 11 is a circuit diagram specifically illustrating a first optical sensor and a read-out circuit. FIG. 12 is a waveform diagram illustrating a scan write signal and signals of the read-out circuit of FIG. 10 according to a light sensing period.

Referring to FIGS. 10 and 11, the read-out circuit 300 may be connected to the optical sensor PS through the light sensing line FRL. For example, the read-out circuit 300 may be connected to the first to fourth optical sensors PS1 to PS4 through one light sensing line FRL. FIG. 10 is a circuit diagram illustrating a relationship between the read-out circuit 300 and the first optical sensor PS1 among the first to fourth optical sensors PS1 to PS4 of FIG. 9. Reference numerals given to the optical sensor PS are the same as those described with reference to FIG. 5, and thus will be omitted.

The read-out circuit 300 may include an amplifier 310 connected to the light sensing line FRL, a sampling unit 320 for holding the output voltage of the amplifier 310, and an analog-digital (AD) converter 330 for converting an analog signal corresponding to the output voltage into digital data.

The amplifier 310 may include a first operational amplifier OA1, a feedback capacitor Cfb, and a feedback reset switch SWRO. The first operational amplifier OA1 may include a first input terminal (−), a second input terminal (+), and an output terminal (out). The first input terminal (−) of the first operational amplifier OA1 may be connected to the light sensing line FRL, the second input terminal (+) of the first operational amplifier OA1 may receive a predetermined initial voltage Vin, and the output terminal (out) of the first operational amplifier OA1 may be connected to the sampling unit 320. An output voltage Vout of the first operational amplifier OA1 may be held in a capacitor of the sampling unit 320. The gain of the first operational amplifier OA1 corresponds to the capacitance of the feedback capacitor Cfb. The feedback capacitor Cfb may accumulate a voltage applied through the light sensing line FRL during one frame period. The applied voltage may be a noise signal voltage or a sensing signal voltage.

The feedback capacitor Cfb and the feedback reset switch SWRO may be connected in parallel between the first input terminal (−) and the output terminal (out) of the first operational amplifier OA1. The feedback reset switch SWRO serves to control the connection of both ends of the feedback capacitor Cfb. When the feedback reset switch SWRO is turned on to connect both ends of the feedback capacitor Cfb, the feedback capacitor Cfb may be reset.

The sampling unit 320 may include a second sampling capacitor Csh2, a first sampling capacitor Csh1, a second sampling switch SW2, and a first sampling switch SW1. The sampling unit 320 may perform sampling of the output voltage Vout of the first operational amplifier OA1 and hold the sampled output voltage in the second sampling capacitor Csh2 and the first sampling capacitor Csh1.

The second sampling capacitor Csh2 may be connected to the output terminal (out) of the first operational amplifier OA1 through the second sampling switch SW2. When the second sampling switch SW2 is turned on, a noise signal voltage (hereinafter, referred to as "Vnoise") may be held in the second sampling capacitor Csh2. The first sampling capacitor Csh1 may be connected to the output terminal (out) of the first operational amplifier OA1 through the first sampling switch SW1. When the first sampling switch SW1 is turned on, the noise signal voltage Vnoise and the sensing signal voltage VC may be held in the first sampling capacitor Csh1.

The AD converter 330 may differentiate and convert the voltage held in the second sampling capacitor Csh2 and the first sampling capacitor Csh1 into digital data. The AD converter 330 may convert the sensing signal voltage VC into light sensing data that is digital data by differentiating the voltage held in the second sampling capacitor Csh2 and the first sampling capacitor Csh1, and output the light sensing data.

Referring further to FIG. 12, there are illustrated the operation process of the feedback reset switch SWRO, the second sampling switch SW2, and the first sampling switch SW1 of the read-out circuit 300 according to the light sensing period ROP and the operation process of the first to fourth scan write signals GW1 to GW4 of the first to fourth optical sensors PS1 to PS4. In other words, as described above, FIG. 11 illustrates the operation process of the read-out circuit 300 connected to a $k^{th}$ light sensing line and $(4k-3)^{th}$ (k being a natural number) to $4k^{th}$ scan write signals applied to the $(4k-3)^{th}$ to $4k^{th}$ scan write lines.

During the light sensing period ROP, the read-out circuit 300 may receive a feedback reset signal IRST, a first sampling signal SHS, a second sampling signal SHR, and a light sensing signal LSS. The read-out circuit 300 may hold the sensing signal voltage VC according to the light sensing signal LSS during the light sensing period ROP.

The light sensing period ROP may be divided into a first read period st1 for resetting the feedback capacitor Cfb according to the feedback reset signal IRST, a second read period st2 for holding a voltage in the second sampling capacitor Csh2 according to the second sampling signal SHR, fifth to eighth read periods st5 to st8 for outputting the light sensing signal LSS generated according to light exposure based on the scan write signal GW input to the read-out circuit 300, and a third read period st3 for holding the sensing signal voltage VC according to the light sensing signal LSS in the first sampling capacitor Csh1 according to the first sampling signal SHS.

The feedback reset signal IRST may control the feedback reset switch SWRO. For example, the feedback reset signal IRST has a first horizontal period HT1. In other words, the interval between pulses of the feedback reset signal IRST may have the first horizontal period HT1. The feedback reset signal LRST may have a turn-on signal during the first read period st1 in the first horizontal period HT1. Accordingly, the turn-on signal of the feedback reset signal IRST may be repeated every first horizontal period HT1.

The feedback reset signal IRST may include the first read period st1 for turning on the feedback reset switch SWRO.

During the first read period st1, the feedback reset switch SWRO is turned on. Accordingly, both ends of the feedback capacitor Cfb may be connected to reset the feedback capacitor Cfb. In the first read period st1, the output voltage Vout of the first operational amplifier OA1 may be equal to the initial voltage Vin of the first input terminal (−).

The second sampling signal SHR may control the second sampling switch SW2. For example, the second sampling signal SHR has the first horizontal period HT1. In other words, the interval between pulses of the second sampling signal SHR may have the first horizontal period HT1. The first horizontal period HT1 of the second sampling signal SHR may partially overlap with the first horizontal period HT1 of the feedback reset signal IRST. The second sampling signal SHR may have the turn-on signal during the second read period st2 in the first horizontal period HT1. Accordingly, the turn-on signal of the second sampling signal SHR may be repeated every first horizontal period HT1.

The second sampling signal SHR may include the second read period st2 for turning on the second sampling switch SW2. During the second read period st2, the feedback reset switch SWRO is turned off, and the second sampling switch SW2 is turned on. Accordingly, the output terminal (out) of the first operational amplifier OA1 may be connected to the second sampling capacitor Csh2. Since the second read period st2 is earlier than the turn-on of the second transistor T2, a valid signal is not outputted through the light sensing line FRL. Accordingly, the noise signal voltage Vnoise may be held in the second sampling capacitor Csh2. In other words, the voltage "Vin+Vnoise" may be held in the second sampling capacitor Csh2.

During the fifth read period st5, the first scan write signal GW1 having the gate-on voltage Von is supplied to the first scan write line GWL1. During the fifth read period st5, the second sensing transistor LT2 of the first optical sensor PS1 is turned on by the first scan write signal GW1. Accordingly, the first sensing transistor LT1 may be connected to the light sensing line FRL, and a first light sensing signal LSS1 (see FIG. 10) that is proportional to the voltage charged in the first node N1 may be outputted to the read-out circuit 300 through the light sensing line FRL. The first light sensing signal LSS1 may be held as a first sensing signal voltage VC1 at the output terminal (out) of the first operational amplifier OA. In other words, the first light sensing signal LSS1 sensed by the first optical sensor PS1 may be held as the first sensing signal voltage VC1 at the amplifier 310.

Further, during the sixth read period st6, the second scan write signal GW2 having the gate-on voltage Von is supplied to the second scan write line GWL2. During the sixth read period st6, the second sensing transistor LT2 of the second optical sensor PS2 is turned on by the second scan write signal GW2. Accordingly, the first sensing transistor LT1 may be connected to the light sensing line FRL, and a second light sensing signal LSS2 (see FIG. 10) that is proportional to the voltage charged in the first node N1 may be outputted to the read-out circuit 300 through the light sensing line FRL. The second light sensing signal LSS2 may be held as the second sensing signal voltage VC2 at the output terminal (out) of the first operational amplifier OA1. In other words, the second light sensing signal LSS2 sensed by the second optical sensor PS2 may be held as the second sensing signal voltage VC2 at the amplifier 310.

Further, during the seventh read period st7, the third scan write signal GW3 having the gate-on voltage Von is supplied to the third scan write line GWL3. During the seventh read period st7, the second sensing transistor LT2 of the third optical sensor PS3 is turned on by the third scan write signal GW3. Accordingly, the first sensing transistor LT1 may be connected to the light sensing line FRL, and the third light sensing signal LSS3 (see FIG. 10) that is proportional to the voltage charged in the first node N1 may be outputted to the read-out circuit 300 through the light sensing line FRL. The third light sensing signal LSS3 may be held as the third sensing signal voltage VC3 at the output terminal (out) of the first operational amplifier OA1. In other words, the third light sensing signal LSS3 sensed by the second optical sensor PS2 may be held as the third sensing signal voltage VC3 at the amplifier 310.

Further, during the eighth read period st8, the fourth scan write signal GW4 having the gate-on voltage Von is supplied to the fourth scan write line GWL4. During the eighth read period st8, the second sensing transistor LT2 of the fourth optical sensor PS4 is turned on by the fourth scan write signal GW4. Accordingly, the first sensing transistor LT1 may be connected to the light sensing line FRL, and the fourth light sensing signal LSS4 (see FIG. 10) that is proportional to the voltage charged in the first node N1 may be outputted to the read-out circuit 300 through the light sensing line FRL. The fourth light sensing signal LSS4 may be held as a fourth sensing signal voltage VC4 at the output terminal (out) of the first operational amplifier OA1. In other words, the fourth light sensing signal LSS4 sensed by the fourth optical sensor PS4 may be held as the fourth sensing signal voltage VC4 at the amplifier 310.

The scan write signal GW has a second horizontal period HT2. The second horizontal period HT2 may be less than the first horizontal period HT1. The scan write signal GW may have the turn-on signal every second horizontal period HT2. In other words, the turn-on signal of the scan write signal GW may be repeated every second horizontal period HT2. For example, the interval between pulses of the first scan write signal GW1 and the second scan write signal GW2 may have the second horizontal period HT2. Further, the interval between pulses of the second to fourth scan write signals GW2 to GW4 may have the second horizontal period HT2.

The first sampling signal SHS may control the first sampling switch SW1. For example, the first sampling signal SHS has the first horizontal period HT1. In other words, the interval between pulses of the first sampling signal SHS may have the first horizontal period HT1. The first sampling signal SHS may have the turn-on signal during the third read period st3 in the first horizontal period HT1. Accordingly, the turn-on signal of the first sampling signal SHS may be repeated every first horizontal period HT1. Further, the feedback reset signal IRST, the second sampling signal SHR, and the first sampling signal SHS may be sequentially turned on.

The first sampling signal SHS may include the third read period st3 for turning on the first sampling switch SW1. During the third read period st3, the first sampling switch SW1 is turned on. Accordingly, the output terminal (out) of the first operational amplifier OA1 may be connected to the first sampling capacitor Csh1. First, during the fifth read period st5 of the third read period st3, the output voltage Vout of the first operational amplifier OA1 corresponds to the first sensing signal voltage VC1, so that the first sensing signal voltage VC1 may be held in the first sampling capacitor Csh1. Next, during the sixth to eighth read periods st6 to st8 of the third read period st3, the output voltage Vout of the first operational amplifier OA1 corresponds to the second to fourth sensing signal voltages VC2 to VC4, so that the second to fourth sensing signal voltages VC2 to VC4 may also be held in the first sampling capacitor Csh1.

Accordingly, the first to fourth sensing signal voltages VC1 to VC4 may be sequentially accumulated and held in the first sampling capacitor Csh1 during the third read period st3.

Further, the first sampling signal SHS includes a fourth read period st4 having a turn-off voltage. During the fourth read period st4, the feedback capacitor Cfb may be reset by the feedback reset signal IRST, and a voltage may be held in the second sampling capacitor Csh2 according to the second sampling signal SHR.

In summary, the first to fourth sensing signal voltages VC1 to VC4 may be accumulated and held in the first sampling capacitor Csh1. In other words, the total amount of the sensing signal voltage VC sensed by the first to fourth optical sensors PS1 to PS4 may be held in the first sampling capacitor Csh1 during the third read period st3. Accordingly, a voltage "Vin+Vnoise+VC" may be held in the first sampling capacitor Csh1.

Then, the AD converter 330 may convert the sensing signal voltage VC into the light sensing data by differentiating the voltage held in the second sampling capacitor Csh2 and the voltage held in the first sampling capacitor Csh1, and may provide the light sensing data to the processor 100 (see FIG. 3).

When the first horizontal period HT1 that is the turn-on period of the feedback reset switch SWRO, the first switch SW1, and the second switch SW2 of the read-out circuit 300 and the second horizontal period HT2 that is the turn-on period of the second sensing transistor LT2 of the optical sensor PS proceed sequentially as shown in FIG. 12, the first horizontal period HT1 may be longer than the second horizontal period HT2.

Further, the third read period st3 in which the first sampling signal SHS has the turn-on voltage may be longer than the second horizontal period HT2. For example, in the third read period st3 the first to fourth optical sensors PS1 to PS4 may sequentially output the light sensing signals LSS in response to the first to fourth scan write signals GW1 to GW4 respectively inputted through the first to fourth scan write lines GWL1 to GWL4. The first to fourth light sensing signals LSS1 to LSS4 may be sequentially outputted to the read-out circuit 300 according to the second horizontal period HT2 (e.g., about 3.47 μs) of the scan write signal GW.

The read-out circuit 300 may output the sensing signal voltage VC once during the first horizontal period HT1 (e.g., about 12.8 μs). For example, the sensing signal voltage VC may be generated every horizontal period HT1 that is the turn-on period of the feedback reset switch SWRO, the first switch SW1, and the second switch SW2 of the read-out circuit 300. In other words, the read-out circuit 300 may generate sensing signal data according to the sensing signal voltage VC every first horizontal period HT1, thereby producing the pulse wave signal.

However, when the scan line connected to the optical sensor PS is the same as the scan line connected to the pixel PX, it is not possible to independently perform the light sensing operation of the optical sensor PS and the image display operation of the pixel PX. In other words, the driving frequency of the read-out circuit 300 is the same as the driving frequency of the display panel 10. Therefore, the third read period st3 in which the first sampling signal SHS has the turn-on voltage is longer than the first horizontal period HT1 of the scan write line GWL, so that at least two light sensing signals LSS may be inputted to the read-out circuit 300. Accordingly, when the interval between the pulses of the first sampling switch SW1 is longer than the interval between the pulses of the scan write signals GW adjacent to each other (e.g., GW1 and GW2), the second sensing transistor LT2 may be turned on by the pulse of the scan write signal GW to apply the plurality of light sensing signals LSS to the light sensing line FRL. Accordingly, a period in which the plurality of light sensing signals LSS are charged in the feedback capacitor Cfb may be increased. Therefore, the capacitance of the feedback capacitor Cfb may increase, so that the plurality of light sensing signals LSS applied to the light sensing line FRL may be sequentially accumulated in the feedback capacitor Cfb. Accordingly, the sensing signal voltage VC according to at least two light sensing signals LSS may be held in the first sampling capacitor Csh1 during the third read period st3.

In summary, the third read period st3 in which the first sampling signal SHS has the turn-on voltage is longer than the first horizontal period HT1 of the scan write signal GW, so that the light sensing signals LSS of the plurality of optical sensors PS may be held in the first sampling capacitor Csh1. Accordingly, the read-out circuit 300 may receive the first to fourth light sensing signals LSS1 to LSS4 of the first to fourth optical sensors PS1 to PS4 and hold the accumulated sensing signal voltage VC. Accordingly, the read-out circuit 300 may produce the pulse wave signal according to the accumulated sensing signal voltage VC.

In the display device 1 according to the present embodiment, even when the light sensing operation of the optical sensor PS and the image display operation of the pixel PX are performed at the same frequency, the read-out circuit 300 may generate the light sensing data according to the light sensing signal LSS of each optical sensor PS. Accordingly, the display device 1 may accurately read the light sensing data.

Figure 13:
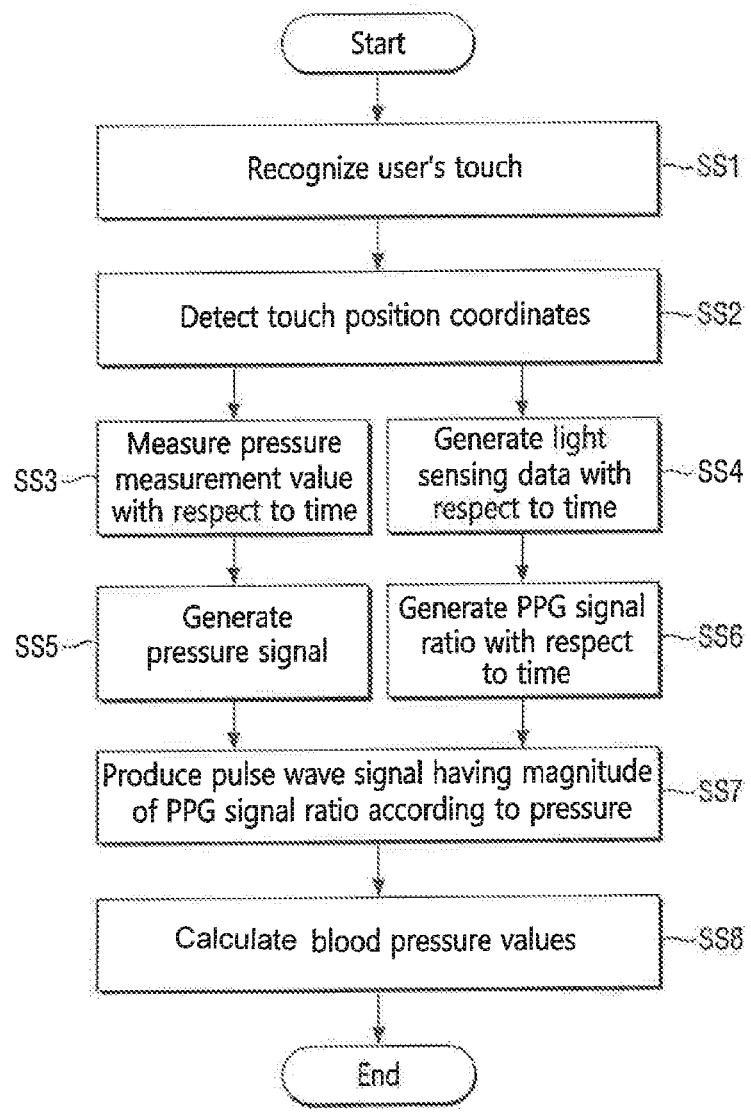
FIG. 13 is a flowchart illustrating a method for measuring a blood pressure in a display device according to one embodiment of the present disclosure.
Figure 14:
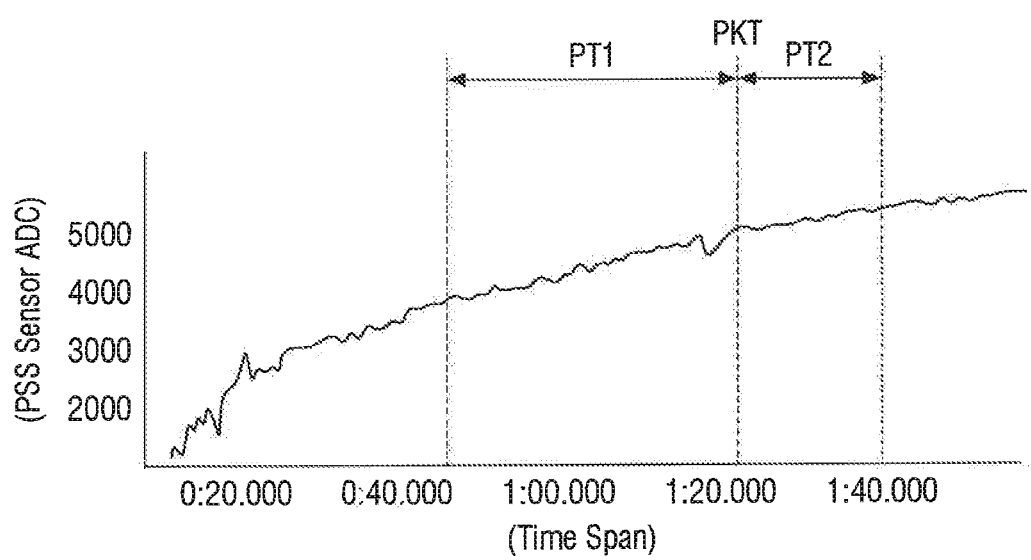
FIG. 14 is a graph showing a pressure measurement value with respect to pressurization time.
Figure 15:
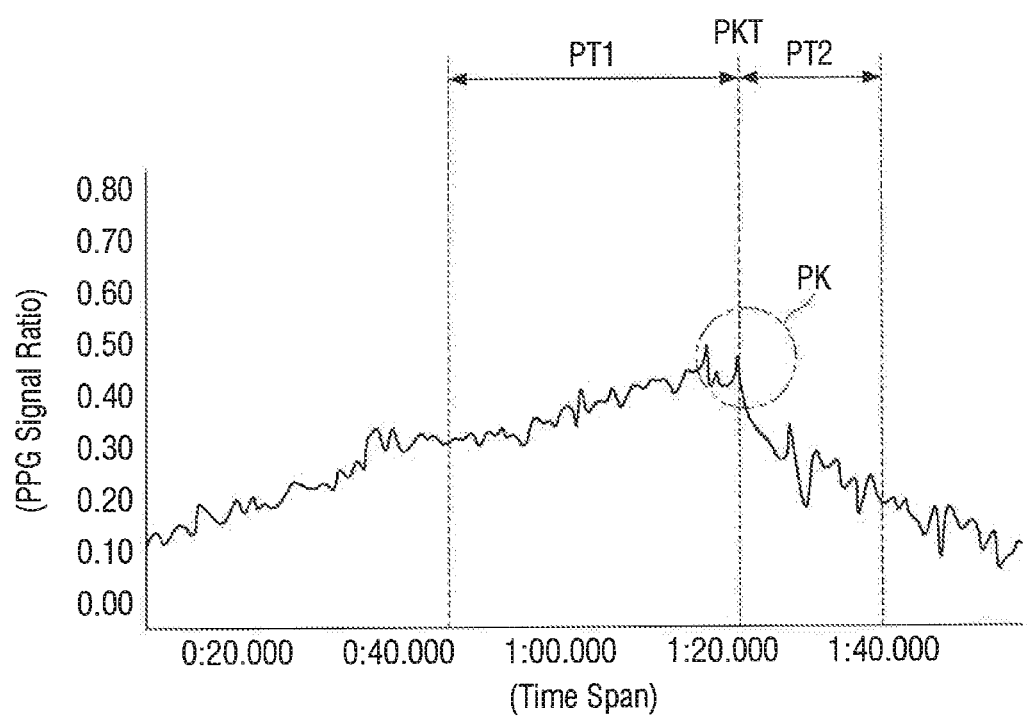
FIG. 15 is a graph illustrating a PPG signal ratio generated according to light sensing data.

FIG. 13 is a flowchart illustrating a method for measuring a blood pressure in a display device according to one embodiment of the present disclosure. FIG. 14 is a graph showing a pressure measurement value with respect to pressurization time. FIG. 15 is a graph illustrating a PPG signal ratio generated according to light sensing data.

Referring to FIGS. 13 to 15, first, the display device 1 may recognize a user's touch (step SS1). The touch sensing unit TSU of the display panel 10 receives touch sensing signals in real time to detect touch data and touch coordinate data (step SS2).

Next, the pressure sensing unit PSU of the display panel 10 may measure a pressure in real time (step SS3). Referring further to FIG. 14, a user may apply a pressure to the pressure sensing unit PSU, and the pressure sensing unit PSU may measure the value of the pressure applied by the user. For example, in a process in which a user touches the display device 1 with a finger, the pressure measurement value measured by the pressure sensor may gradually increase over time and reach a maximum value. When the pressure measurement value (e.g., contact pressure) increases, a blood vessel may constrict and blood flow may be reduced or become zero. Accordingly, the pressure measurement value with respect to time may be outputted to the processor 100. The processor 100 may generate a pressure signal PSS based on the pressure measurement value with respect to time (step SS5).

Meanwhile, the read-out circuit 300 generates light sensing data with respect to time (step SS4).

Referring further to FIG. 15, in order to produce blood pressure information, pulse information with respect to time is also required together with pressure data. When a heart contracts, blood pumped from the left ventricle of the heart moves to peripheral tissues, so that the blood volume on an arterial side increases. Further, when the heart contracts, red blood cells carry more oxyhemoglobin to the peripheral tissues. When the heart relaxes, the heart receives a partial influx of blood from the peripheral tissues. In this case, when the artery is irradiated with the light emitted from the display pixel, the irradiated light may be absorbed by the peripheral tissues. Light absorbance is dependent on hematocrit and blood volume. The light absorbance may have a maximum value when the heart contracts and may have a minimum value when the heart relaxes. Since the light absorbance is in inverse proportion to the amount of light incident on the optical sensor PS, it is possible to estimate the light absorbance at a corresponding time point from light receiving data of the amount of light incident on the optical sensor PS.

Therefore, as described above, the optical sensor PS outputs the light sensing signals LSS to the light sensing lines FRL in response to the scan write signal GW. Accordingly, the read-out circuit 300 receives the light sensing signals LSS from the light sensing lines FRL corresponding to a touch area. The read-out circuit 300 may convert the received light sensing signals LSS into a light data signal to generate light sensing data. The read-out circuit 300 may output the generated light sensing data to the processor 100. The processor 100 may receive the light sensing data from the read-out circuit 300 and generate a PPG signal ratio with respect to time (step SS6).

Accordingly, the processor 100 produces the pulse wave signal according to the pressure applied by the user based on the pressure signal PSS, which is produced by the pressure sensing unit PSU and converted digitally, and the PPG signal ratio with respect to time, which is sensed by the optical sensor PS (step SS7). The pulse wave signal may have a waveform vibrating according to the cardiac cycle.

The processor 100 may estimate blood pressure values of finger blood vessels based on time differences between time points PKT corresponding to peaks PK of the produced pulse wave signal and time points corresponding to peaks of the filtered pulse wave. For example, the read-out circuit 300 may produce pulse wave signals for preset periods PT1 and PT2 before and after the time points PKT corresponding to the peaks PK of the produced pulse wave signals and detect a blood pressure according to the differences between the pulse wave signals. Among the estimated blood pressure values, a maximum blood pressure value may be determined as a systolic blood pressure value, and a minimum blood pressure value may be determined as a diastolic blood pressure value. Further, additional blood pressure values such as an average blood pressure value or the like may be calculated using the estimated blood pressure values (step SS8).

The method for measuring the blood pressure described above is just an example, various other methods are disclosed in Korean Patent Application Publication No. 10-2018-0076050, Korean Patent Application Publication No. 10-2017-0049280, and Korean Patent Application Publication No. 10-2019-0040527, the disclosures of which are incorporated by reference herein in their entireties.

In the display device 1 according to the present embodiment, the optical sensor PS is driven at the same frame frequency as that of the pixel PX, and the light sensing signal LSS sensed by each optical sensor PS is accumulated and held, thereby preventing a decrease in the frame frequency of the light sensing signal LSS measured by the optical sensor PS. Accordingly, it is possible to accurately produce user's blood pressure information.

Figure 16:
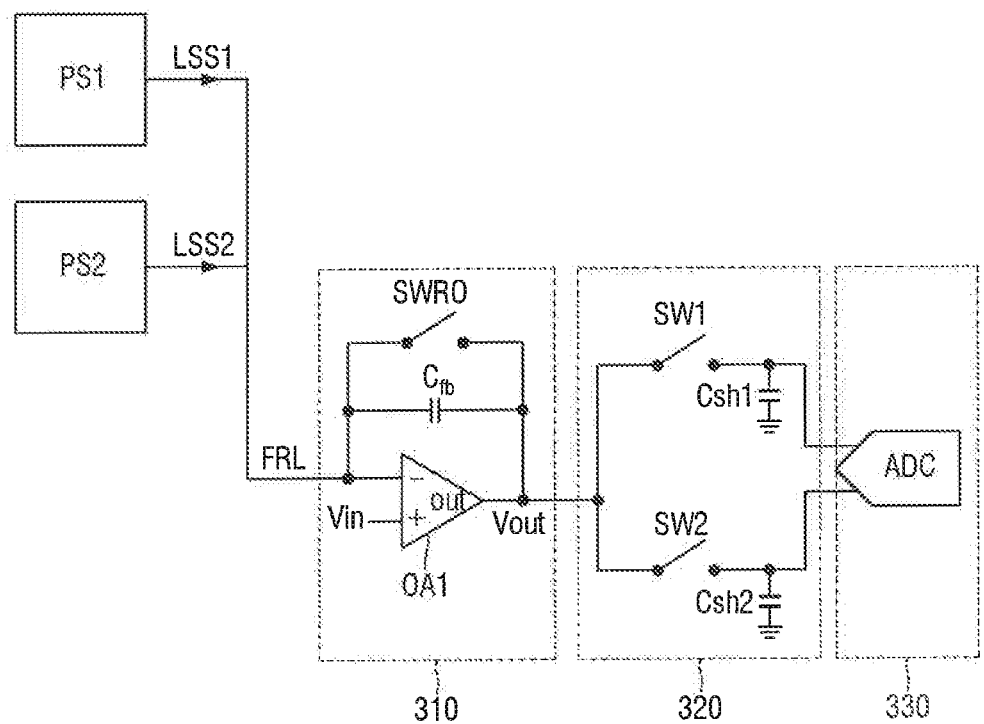
FIG. 16 is a block diagram illustrating an optical sensor and a read-out circuit according to another embodiment of the present disclosure.
Figure 17:
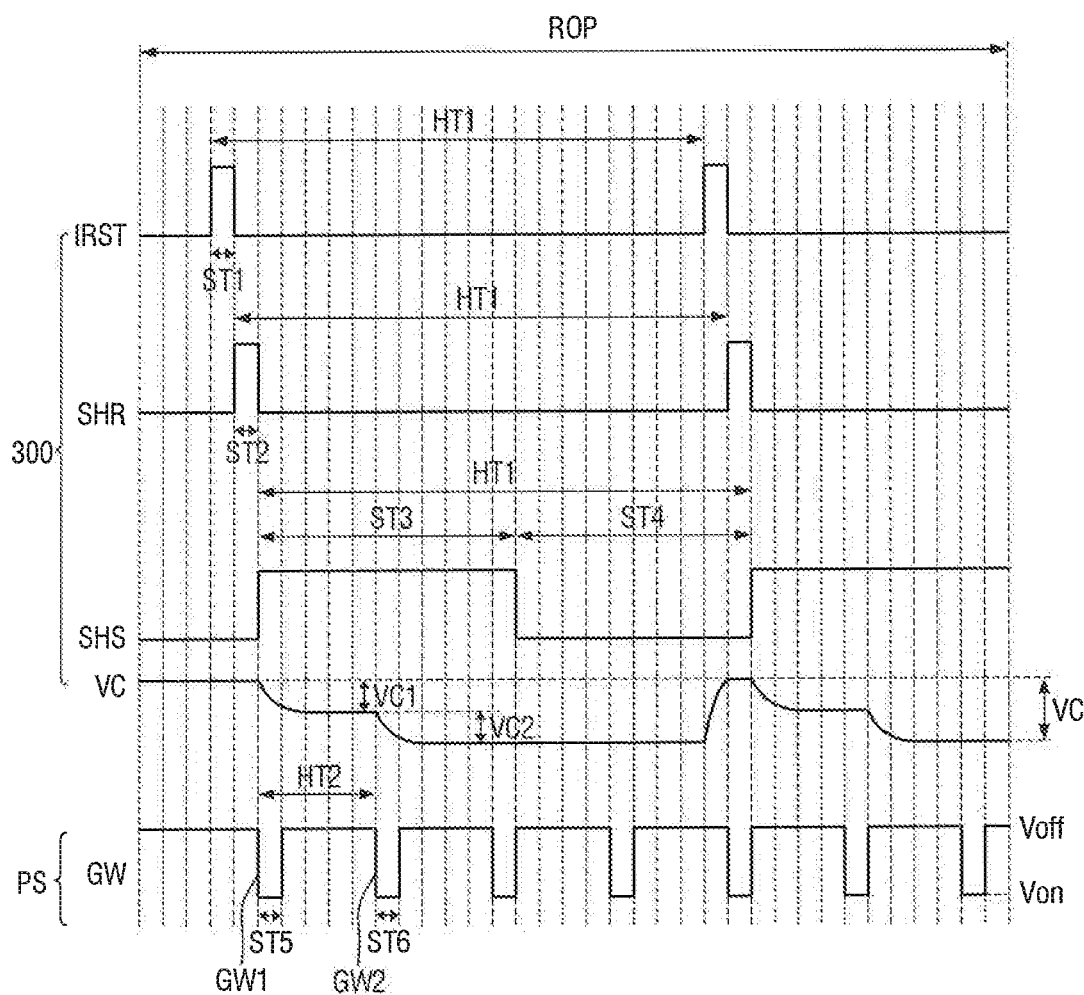
FIG. 17 is a waveform diagram illustrating a scan write signal and signals of the read-out circuit of FIG. 16 according to a light sensing period.

FIG. 16 is a block diagram illustrating an optical sensor and a read-out circuit according to another embodiment of the present disclosure. FIG. 17 is a waveform diagram illustrating a scan write signal and signals of the read-out circuit of FIG. 16 according to a light sensing period.

The embodiment of FIGS. 16 and 17 is substantially the same as the embodiment of FIGS. 10 to 12 except for the length of the third read period st3 of the first sampling signal SHS, so that the differences from the embodiment of FIGS. 10 to 12 will be mainly described.

Referring to FIG. 16, the read-out circuit 300 may be connected to the optical sensor PS through the light sensing line FRL. For example, the read-out circuit 300 may be connected to the first and second optical sensors PS1 and PS2 through one light sensing line FRL. The read-out circuit 300 may receive the first light sensing signal LSS1 of the first optical sensor PS1 and the second light sensing signal LSS2 of the second optical sensor PS2.

The read-out circuit 300 may include an amplifier 310 connected to the light sensing line FRL, a sampling unit 320 for holding the output voltage of the amplifier 310, and an analog-digital (AD) converter 330 for converting an analog signal corresponding to the output voltage to digital data. The description of the read-out circuit 300 is the same as the description in FIG. 10, and thus will be omitted.

Referring further to FIG. 17, there are illustrated the operation processes of the feedback reset switch SWRO, the second sampling switch SW2, and the first sampling switch SW1 of the read-out circuit 300 according to the light sensing period ROP and the operation processes of the first to fourth scan write signals GW1 to GW4 of the first to fourth optical sensors PS1 to PS4. In other words, as described above, FIG. 17 illustrates the operation process of the read-out circuit 300 connected to the $k^{th}$ (k being a natural number) light sensing line and the $(4k-3)^{th}$ to $4k^{th}$ scan write signals applied to the $(4k-3)^{th}$ and $(4k-2)^{th}$ scan write lines.

During the light sensing period ROP, the read-out circuit 300 may receive the feedback reset signal IRST, the first sampling signal SHS, the second sampling signal SHR, and the light sensing signal LSS. The read-out circuit 300 may hold the sensing signal voltage VC according to the light sensing signal LSS during the light sensing period ROP.

The light sensing period ROP may be divided into the first read period st1 for resetting the feedback capacitor Cfb according to the feedback reset signal IRST, the second read period st2 for holding a voltage in the second sampling capacitor Csh2 according to the second sampling signal SHR, the fifth and sixth read periods st5 and st6 for outputting the light sensing signal LSS generated according to light exposure based on the scan write signal GW to the read-out circuit 300, and the third read period st3 for holding the sensing signal voltage VC according to the light sensing signal LSS in the first sampling capacitor Csh1 according to the first sampling signal SHS. The description of the first read period st1, the second read period st2 of the second sampling signal SHR, and the fifth and sixth read periods st5 and st6 of the scan write signal GW is the same as the description in FIG. 10, and thus will be omitted.

The first sampling signal SHS may include the third read period st3 for turning on the first sampling switch SW1. During the third read period st3, the first sampling switch SW1 is turned on. Accordingly, the output terminal (out) of the first operational amplifier OA1 may be connected to the first sampling capacitor Csh1. First, during the fifth read period st5 of the third read period st3, the output voltage Vout of the first operational amplifier OA1 corresponds to the first sensing signal voltage VC1, so that the first sensing signal voltage VC1 may be held in the first sampling capacitor Csh1. Next, during the sixth read period st6 of the third read period st3, the output voltage Vout of the first operational amplifier OA1 corresponds to the second sensing signal voltage VC2, so that the second sensing signal voltage VC2 may also be held in the first sampling capacitor Csh1. Accordingly, the first and second sensing signal voltages VC1 to VC2 may be sequentially accumulated and held in the first sampling capacitor Csh1 during the third read period st3.

Also in the present embodiment, the third read period st3 in which the first sampling signal SHS has the turn-on voltage is longer than the first horizontal period HT1 of the scan write line GWL, so that at least two light sensing signals LSS may be inputted to the read-out circuit 300. However, compared to the embodiment of FIG. 12, the third read period st3 of FIG. 17 is shorter. Accordingly, in the display device 1 according to the present embodiment, even when the light sensing operation of the optical sensor PS and the image display operation of the pixel PX are performed at the same frequency, the read-out circuit 300 may generate the light sensing data according to the light sensing signal LSS of each optical sensor PS. Accordingly, the display device 1 may accurately read the light sensing data.

Figure 18:
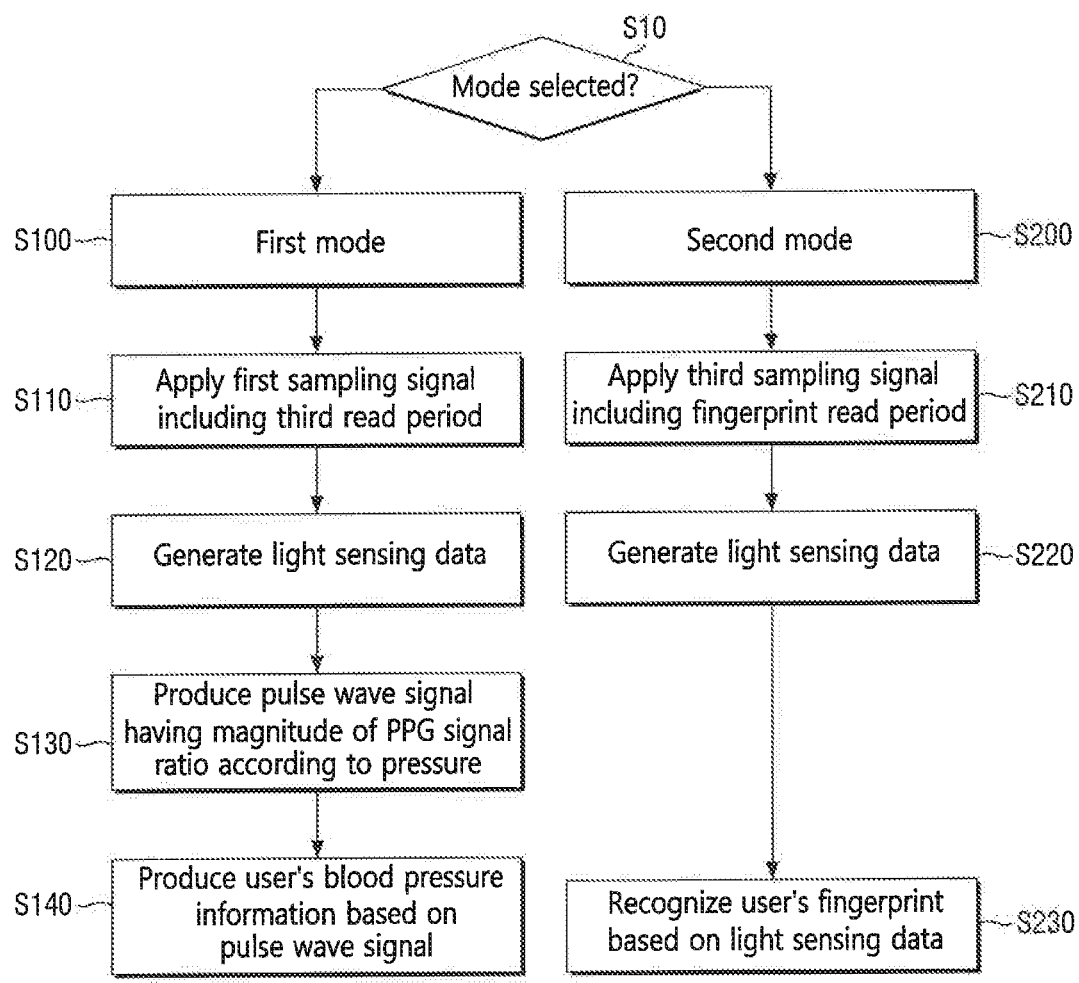
FIG. 18 is a flowchart illustrating a method for measuring a blood pressure and a fingerprint in a display device according to another embodiment of the present disclosure.
Figure 19:
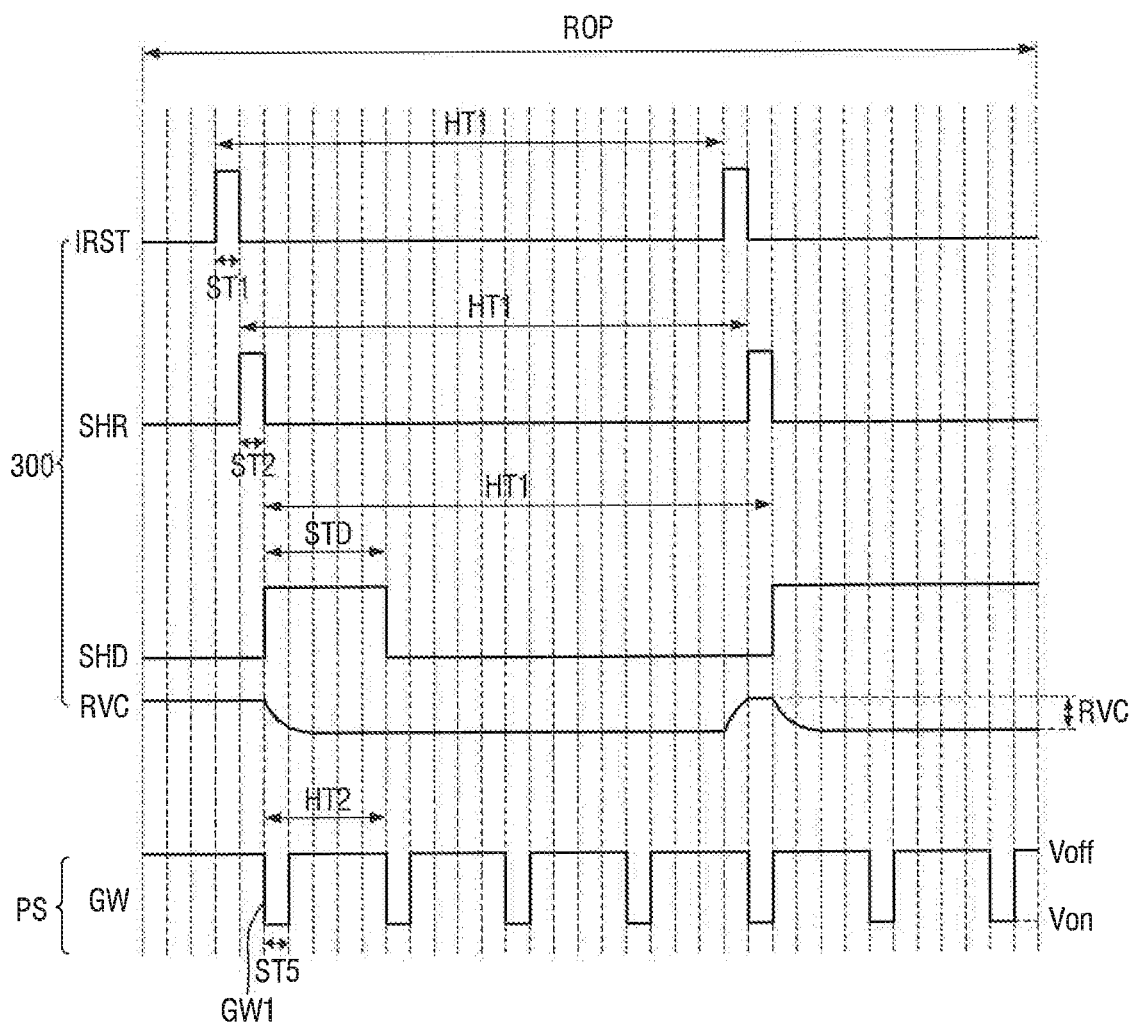
FIG. 19 is a waveform diagram illustrating a scan write signal and signals of a read-out circuit according to a light sensing period in a second mode according to another embodiment of the present disclosure.

FIG. 18 is a flowchart illustrating a method for measuring a blood pressure and a fingerprint in a display device according to another embodiment of the present disclosure. FIG. 19 is a waveform diagram illustrating a scan write signal and signals of a read-out circuit according to a light sensing period in a second mode according to another embodiment of the present disclosure.

The embodiment of FIGS. 18 and 19 in which a user's blood pressure information is produced in a first mode and a user's fingerprint is recognized in a second mode is different from the embodiment of FIGS. 10 to 15 in which a user's blood pressure information is produced. Accordingly, the differences between the embodiment of FIGS. 18 and 19 and the embodiment of FIGS. 10 to 15 will be mainly described.

Referring to FIG. 18, first, a user may select a mode (step S10).

When the first mode is selected (step S100), the timing controller 210 may apply the first sampling signal SHS including the third read period to the read-out circuit 300 (step S110). Accordingly, the read-out circuit 300 may generate light sensing data (step S120), and may output the generated light sensing data to the processor 100.

In the first mode, the read-out circuit 300 may receive the feedback reset signal IRST, the first sampling signal SHS, the second sampling signal SHR, and the light sensing signal LSS during the light sensing period ROP. The read-out circuit 300 may hold the sensing signal voltage VC according to the light sensing signal LSS during the light sensing period ROP.

The light sensing period ROP may be divided into the first read period st1 for resetting the feedback capacitor Cfb according to the feedback reset signal IRST, the second read period st2 for holding a voltage in the second sampling capacitor Csh2 according to the second sampling signal SHR, the fifth read period st5 for outputting the light sensing signal LSS generated according to light exposure based on the scan write signal GW to the read-out circuit 300, and the third read period st3 for holding the sensing signal voltage VC according to the light sensing signal LSS in the first sampling capacitor Csh1 according to the first sampling signal SHS. The description of the first read period st1, the second read period st2 of the second sampling signal SHR, the third read period st3 of the first sampling signal SHS, and the fifth read period st5 of the scan write signal GW is the same as the description in FIG. 10, and thus will be omitted.

Accordingly, the first to fourth light sensing signals LSS1 to LSS4 respectively generated by the first to fourth optical sensors PS1 to PS4 may be held in the first sampling capacitor Csh1 during the third read period st3 of the first sampling signal SHS. In other words, the first to fourth sensing signal voltages VC1 to VC4 may be accumulated and held in the first sampling capacitor Csh1.

Next, in the first mode, the processor 100 produces a pulse wave signal having a magnitude of the PPG signal ratio according to a pressure based on the pressure signal PSS inputted from the pressure sensing unit PSU and the light sensing data inputted from the read-out circuit 300 (step S130). Then, the processor 100 may produce the user's blood pressure information based on the pulse wave signal (step S140). The description thereof is substantially the same as the description in FIGS. 13 to 15, and thus will be omitted.

When the second mode is selected (step S200), the timing controller 210 may apply a third sampling signal SHD including a fingerprint read period to the read-out circuit 300 (step S210). Accordingly, the read-out circuit 300 may generate light sensing data (step S220), and may output the generated light sensing data to the processor 100.

Referring further to FIG. 19, in the second mode, the read-out circuit 300 may receive the feedback reset signal IRST, the third sampling signal SHD, the second sampling signal SHR, and the light sensing signal LSS during the light sensing period ROP. The read-out circuit 300 may hold the sensing signal voltage VC according to the light sensing signal LSS during the light sensing period ROP.

The light sensing period ROP may be divided into the first read period st1 for resetting the feedback capacitor Cfb according to the feedback reset signal IRST, the second read period st2 for holding a voltage in the second sampling capacitor Csh2 according to the second sampling signal SHR, the fifth read period st5 for outputting the light sensing signal generated according to light exposure based on the scan write signal GW to the read-out circuit 300, and the fingerprint read period STD for holding a fingerprint sensing signal voltage RVC according to the light sensing signal in the first sampling capacitor Csh1 according to the third sampling signal SHD. The description of the first read period st1, the second read period st2 of the second sampling signal SHR, and the fifth read period st5 of the scan write signal GW are the same as the description in FIG. 10, and thus will be omitted.

The third sampling signal SHD may control the first sampling switch SW1. For example, the third sampling signal SHD has the first horizontal period HT1. In other words, the interval between pulses of the third sampling signal SHD may have the first horizontal period HT1. The third sampling signal SHD may have the turn-on signal during the fingerprint read period STD in the first horizontal period HT1. Accordingly, the turn-on signal of the third sampling signal SHD may be repeated every first horizontal period HT1. Further, the feedback reset signal IRST, the second sampling signal SHR, and the third sampling signal SHD may be sequentially turned on.

The third sampling signal SHD may include the fingerprint read period STD for turning on the first sampling switch SW1. During the fingerprint read period STD, the first sampling switch SW1 is turned on. Accordingly, the output terminal (out) of the first operational amplifier OA1 may be connected to the first sampling capacitor Csh1. First, during the fifth read period st5 of the fingerprint read period STD, the output voltage Vout of the first operational amplifier OA1 corresponds to the fingerprint sensing signal voltage RVC, so that the fingerprint sensing signal voltage RVC may be held in the first sampling capacitor Csh1.

The scan write signal GW has the second horizontal period HT2. The scan write signal GW may have the turn-on signal every second horizontal period HT2. In other words, the turn-on signal of the scan write signal GW may be repeated every second horizontal period HT2. For example, the interval between the pulses of the first scan write signal GW1 and the second scan write signal GW2 may have the second horizontal period HT2. Further, the interval between the pulses of the second to fourth scan write signals GW2 to GW4 may have the second horizontal period HT2.

When the first horizontal period HT1 that is the turn-on period of the feedback reset switch SWRO, the first switch SW1, and the second switch SW2 of the read-out circuit 300 and the second horizontal period HT2 that is the turn-on period of the second sensing transistor LT2 of the optical sensor PS proceed sequentially as shown in FIG. 19, the first horizontal period HT1 may be longer than the second horizontal period HT2.

Further, the fingerprint read period STD in which the third sampling signal SHD has the turn-on voltage may be the same as the second horizontal period HT2. For example, each optical sensor PS may sequentially output a light sensing signal in response to the scan write signal GW inputted through the scan write line GWL. The light sensing signal may be sequentially outputted to the read-out circuit 300 according to the second horizontal period HT2 (e.g., about 3.47 μs) of the scan write signal GW.

The read-out circuit 300 may output the sensing signal voltage VC once during the first horizontal period HT1 (e.g., about 12.8 μs). For example, the sensing signal voltage VC may be generated every first horizontal period HT1 that is the turn-on period of the feedback reset switch SWRO, the first switch SW1, and the second switch SW2 of the read-out circuit 300. In other words, the read-out circuit 300 may generate sensing signal data according to the fingerprint sensing signal voltage RVC every first horizontal period HT1, thereby producing a pulse wave signal.

The fingerprint read period STD in which the third sampling signal SHD has the turn-on voltage may be the same as the second horizontal period HT2 of the scan write line GWL. As described above, when the scan line connected to the optical sensor PS is the same as the scan line connected to the pixel PX, the light sensing operation of the optical sensor PS and the image display operation of the pixel PX cannot be performed independently. Accordingly, the fingerprint read period STD in which the third sampling signal SHD has the turn-on voltage is the same as the second horizontal period HT2 of the scan write line GWL, so that the read-out circuit 300 may receive one light sensing signal during the fingerprint read period STD. In this case, since the fingerprint read period STD is the same as the second horizontal period HT2, the frame frequency in the second mode for detecting a fingerprint may be different from that in the first mode.

Then, the AD converter 330 may convert the sensing signal voltage VC into light sensing data by differentiating the voltage held in the second sampling capacitor Csh2 and the voltage held in the first sampling capacitor Csh1, and may provide the light sensing data to the processor 100 (see FIG. 3).

In summary, the fingerprint read period STD in which the third sampling signal SHD has the turn-on voltage is the same as the second horizontal period H T2 of the scan writing signal GW, so that the light sensing signal of one optical sensor PS may be held in the first sampling capacitor Csh1. Therefore, the read-out circuit 300 may hold the fingerprint sensing signal voltage RVC, and accordingly, the read-out circuit 300 may produce a pulse wave signal according to the held fingerprint sensing signal voltage RVC.

In the display device 1 according to the present embodiment, in the second mode, the read-out circuit 300 may generate light sensing data according to the light sensing signal of each optical sensor PS. Even if the driving frequency of the optical sensor PS in the second mode is lower than the driving frequency of the optical sensor PS in the first mode, it is possible to generate high-resolution light sensing data because the light sensing data is generated according to the light sensing signal sensed by each optical sensor PS. In other words, the high-resolution light sensing data may be generated according to the third sampling signal SHD of the second mode. Accordingly, as will be described later, the display device 1 may accurately read the light sensing data.

Finally, in the second mode, the processor 100 may recognize a user's fingerprint based on the light sensing data inputted from the read-out circuit 300 (step S230). The processor 100 may determine ridges of the fingerprint of the light sensing data or valleys between the ridges and may sense the user's fingerprint. Accordingly, the processor 100 may analyze the fingerprint sensing data and determine whether or not a preset fingerprint matches the user's fingerprint by comparing both fingerprints. When the preset fingerprint and the fingerprint sensing data transmitted from the read-out circuit 300 are the same, preset functions may be performed.

In the present embodiment, it is possible to control the resolution and the frequency of the light sensing data by differently controlling the third read period st3 of the first sampling signal SHS in the first mode and the fingerprint read period STD of the third sampling signal SHD in the second mode. In other words, since the driving frequency of the optical sensor PS in the second mode is lower than the driving frequency of the optical sensor PS in the first mode, the read-out circuit 300 may generate high-frequency light sensing data in the first mode, and may generate high-resolution light sensing data in the second mode. Accordingly, it is possible to accurately produce the user's blood pressure information in the first mode and accurately produce the user's fingerprint in the second mode.

Figure 20:
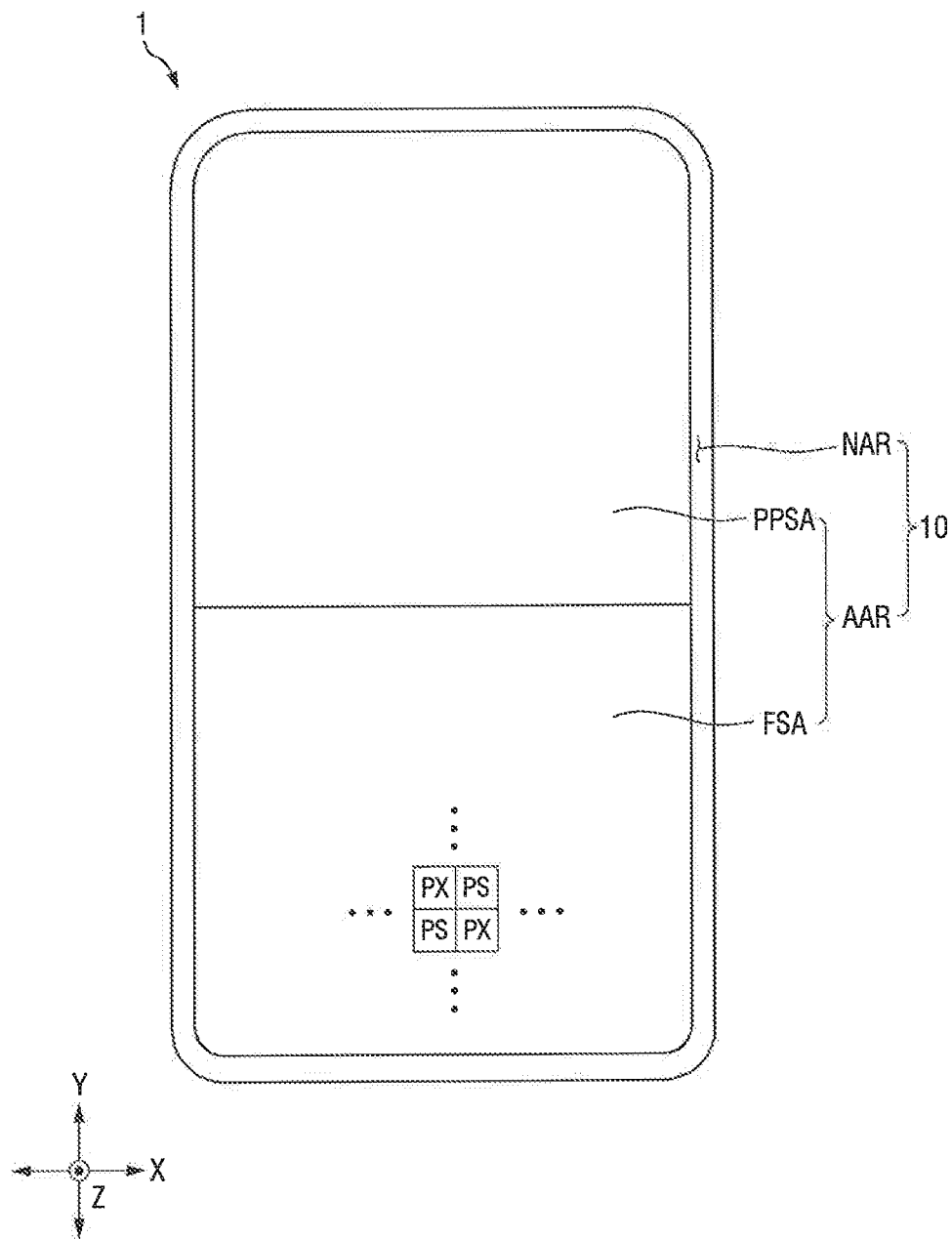
FIGS. 20 and 21 are plan views illustrating a display device according to still another embodiment of the present disclosure.
Figure 21:
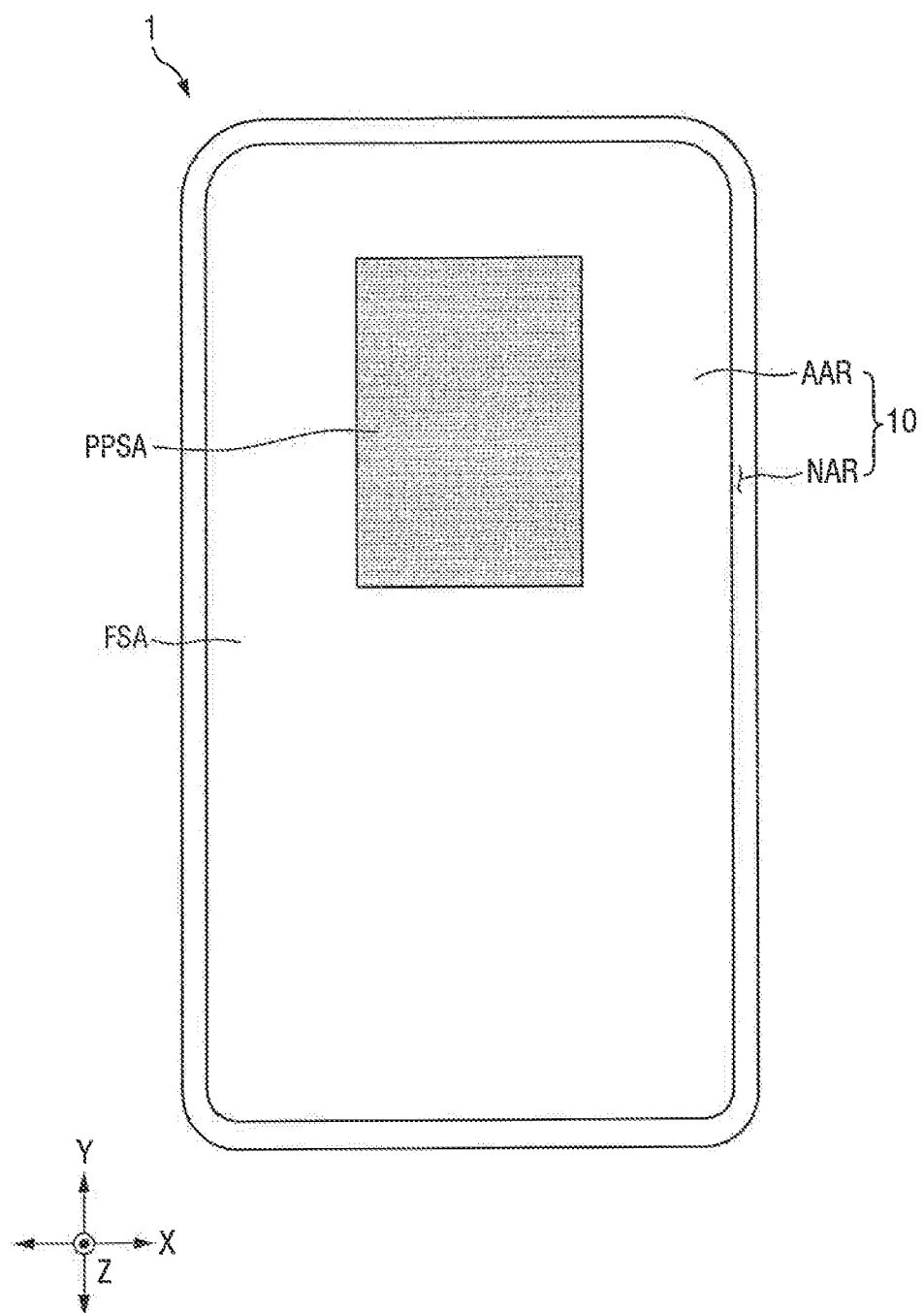

FIGS. 20 and 21 are plan views illustrating a display device according to still another embodiment of the present disclosure.

Referring to FIGS. 20 and 21, the active region AAR of the display panel 10 may include a fingerprint sensing area FSA and the light sensing area PPSA.

The light sensing area PPSA is a region that reacts to light, and is configured to sense the amount or wavelength of incident light. The light sensing area PPSA may overlap the display area. As described above, the light sensing area PPSA may be a region for measuring a blood pressure. Accordingly, the first sampling signal SHS may be applied to the read-out circuit 300 connected to the optical sensor PS of the light sensing area PPSA.

The fingerprint sensing area FSA is a region that reacts to light, and is configured to sense the amount or wavelength of incident light. The fingerprint sensing area FSA may overlap the display area. As described above, the fingerprint sensing area FSA may be a region for detecting a fingerprint. Accordingly, the third sampling signal SHD may be applied to the read-out circuit 300 connected to the optical sensor PS of the fingerprint sensing area FSA.

The light sensing area PPSA and the fingerprint sensing area FSA may be adjacent to each other. For example, as in the case of FIG. 20, the light sensing area PPSA may be disposed on the upper area of the active region AAR, and the fingerprint sensing area FSA may be disposed on the lower area of the active region AAR. Alternatively, as in the case of FIG. 21, the light sensing area PPSA may be disposed only in a limited area required for blood pressure measurement. In this case, the light sensing area PPSA may overlap a part of the display area, but may not overlap another part of the display area.

The plurality of optical sensors PS responding to light may be disposed in the light sensing area PPSA and the fingerprint sensing area FSA. The description thereof is substantially the same as that in the embodiment of FIGS. 1 to 10, and thus will be omitted.

In concluding the detailed description, those skilled in the art will appreciate that many variations and modifications can be made to the disclosed embodiments without substantially departing from the scope of the present disclosure. Therefore, the disclosed embodiments are not for purposes of limitation.

What is claimed is:

1. A display device, comprising:
 a display panel comprising scan write lines, sensing lines, pixels respectively connected to the scan write lines, and optical sensors respectively connected to the scan write lines and the sensing lines;
 a scan driver configured to sequentially output scan write signals to the scan write lines in response to a scan control signal;
 a read-out circuit configured to receive light sensing signals of the optical sensors from the sensing lines in response to a first sampling signal; and
 a timing controller configured to control the scan driver and the read-out circuit,
 wherein an interval between pulses of the first sampling signal has a first horizontal period, and an interval between pulses of each of the scan write signals has a second horizontal period,
 wherein each of the optical sensors comprises:
 a photoelectric conversion element comprising an anode electrode and a cathode electrode connected to a voltage line;
 a first sensing transistor comprising a gate electrode connected to the anode electrode of the photoelectric conversion element,
 a reset transistor configured to connect a reset voltage line to the anode electrode of the photoelectric conversion element in response to a reset signal; and
 a second sensing transistor configured to connect the first sensing; transistor to a corresponding one of the sensing lines in response to the scan write signal input thereto,
 wherein the read-out circuit comprises:
 an amplifier connected to the corresponding one of the sensing lines and comprising an operational amplifier,
 a sampling unit comprising a first sampling capacitor configured to hold a voltage of one of the light sensing signals in response to the first sampling signal; and
 an analog-digital (AD) converter configured to convert the held light sensing signal voltage into digital data,
 wherein each of the second sensing transistors is turned on in response to a corresponding one of the scan write signals to output a sensing signal voltage through the sensing line to which it is connected, and each of the sensing signal voltages is held in the first sampling capacitor in response to the first sampling signal, wherein the first sampling signal has a first period in which the first sampling capacitor is turned on and a second period in which the first sampling capacitor is turned off, wherein in the first period, the first sampling capacitor accumulates and holds at least two sensing signal voltages among the sensing signal voltages, the at least two sensing signal voltages including a first sensing signal voltage output from a first optical sensor connected to a first scan write line and a second sensing signal voltage output from a second optical sensor connected to a second scan write line.

2. The display device of claim 1, wherein the first horizontal period is longer than the second horizontal period.

3. The display device of claim 1, further comprising a reset driver configured to output the reset signal for turning on each reset transistor of the optical sensors.

4. The display device of claim 1, wherein the first period is longer than the second horizontal period.

5. The display device of claim 1, wherein the sampling unit further comprises a second sampling capacitor configured to hold a noise voltage in response to a second sampling signal, and the second sampling signal and the first sampling signal are sequentially turned on.

6. The display device of claim 5, wherein an interval between pulses of each of the second sampling signals is equal to the first horizontal period.

7. The display device of claim 1, wherein the optical sensors comprise the first optical sensor and the second optical sensor, and the scan write lines comprise:

the first scan write line configured to provide an $n^{th}$ scan write signal (n being a positive integer) to the pixel connected to the first optical sensor and the first optical sensor; and the second scan write line configured to provide an $(n+1)^{th}$ scan write signal to the pixel connected to the second optical sensor and the second optical sensor, wherein the second horizontal period between the $n^{th}$ scan write signal and the $(n+1)^{th}$ scan write signal is shorter than the first horizontal period of the first sampling signal.

8. The display device of claim 1, wherein the timing controller outputs a first sampling signal having a turn-on voltage during the first period in a first mode for detecting a fingerprint and having a turn-on voltage during the second period in a second mode for detecting a blood pressure, and the first period is shorter than the second period.

9. The display device of claim 8, wherein the first period is shorter than the second horizontal period.

10. The display device of claim 9, wherein the second horizontal period is shorter than the second period.

11. A display device, comprising:

a display panel comprising a pixel, a first optical sensor, and a second optical sensor;

first scan write lines configured to provide a first scan write signal to the pixel and the first optical sensor;

second scan write lines configured to provide a second scan write signal to the pixel and the second optical sensor;

a scan driver configured to output the first scan write signal to the first scan write lines and the second scan write signal to the second scan write lines;

a read-out circuit configured to receive a first light sensing signal from the first optical sensor through a first sensing line in response to a first sampling signal, and receive a second light sensing signal from the second light sensor through a second sensing line; and a timing controller configured to output the first sampling signal to the read-out circuit, wherein the first sampling signal has a first horizontal period, and a pulse width of each of the first scan write signal and the second scan write signal has a second horizontal period, wherein the first horizontal period is longer than the second horizontal period, wherein the first sampling signal has a first period having a turn-on voltage and a second period having a turn-off voltage, and the read-out circuit is configured to accumulate and receive the first and second light sensing signals in the first period, wherein the read-out circuit comprises:

an amplifier connected to the first and second sensing lines and comprising an operational amplifier;

a sampling unit comprising a first sampling capacitor configured to accumulate and hold voltages of the first and second light sensing signals during the first period of the first sampling signal; and an analog-digital (AD) converter configured to convert the held voltages of the first and second light sensing signals into digital data, wherein the first sampling capacitor is turned on in the first period of the first sampling signal and turned off in a second period of the first sampling signal, wherein in the first period, the first sampling capacitor accumulates and holds at least two sensing signal voltages corresponding to the first and second light sensing signals, the at least two sensing signal voltages including a first sensing signal voltage output from the first optical sensor connected to the first scan write lines and a second sensing signal voltage output from the second optical sensor connected to the second scan write lines.

12. The display device of claim 11, wherein the first period is longer than the second horizontal period.

13. A display device, comprising:

a display panel comprising scan write lines, sensing lines, pixels respectively connected to the scan write lines, and optical sensors respectively connected to the scan write lines and the sensing lines;

a scan driver configured to sequentially output scan write signals to the scan write lines in response to a scan control signal;

a read-out circuit configured to receive light sensing signals of the optical sensors from the sensing lines in response to a first sampling signal; and a timing controller configured to control the scan driver and the read-out circuit, wherein the first sampling signal has a first horizontal period, and each of the scan write signals has a second horizontal period, wherein the first and second horizontal periods overlap each other and the first horizontal period is longer than the second horizontal period, wherein the first sampling signal has a first period in which a first sampling capacitor of the read-out circuit is turned on and a second period in which the first sampling capacitor is turned off, wherein in the first period the first sampling capacitor accumulates and holds at least two sensing signal voltages corresponding to the light sensing signals, the at least two sensing, signal voltages including a first sensing signal voltage output from a first optical sensor connected to a first scan write line and a second sensing signal voltage output from a second optical sensor connected to a second scan write line.

* * * * *